US012416011B2

(12) United States Patent
Maselko et al.

(10) Patent No.: US 12,416,011 B2
(45) Date of Patent: *Sep. 16, 2025

(54) BIOCONTAINMENT/BIOCONTROL SYSTEM AND METHODS

(71) Applicant: REGENTS OF THE UNIVERSITY OF MINNESOTA, Minneapolis, MN (US)

(72) Inventors: Maciej Maselko, Sydney (AU); Mike Smanski, Falcon Heights, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 206 days.

This patent is subject to a terminal disclaimer.

(21) Appl. No.: 18/219,524

(22) Filed: Jul. 7, 2023

(65) Prior Publication Data
US 2024/0093215 A1    Mar. 21, 2024

Related U.S. Application Data

(63) Continuation of application No. 15/775,164, filed as application No. PCT/US2016/061297 on Nov. 10, 2016, now Pat. No. 11,718,858.

(60) Provisional application No. 62/253,954, filed on Nov. 11, 2015.

(51) Int. Cl.
| | |
|---|---|
| *C12N 15/63* | (2006.01) |
| *C12N 1/14* | (2006.01) |
| *C12N 1/18* | (2006.01) |
| *C12N 9/22* | (2006.01) |
| *C12N 15/80* | (2006.01) |
| *C12N 15/81* | (2006.01) |
| *C12N 15/82* | (2006.01) |
| *C07K 14/005* | (2006.01) |

(52) U.S. Cl.
CPC .......... *C12N 15/8218* (2013.01); *C12N 1/14* (2013.01); *C12N 1/18* (2013.01); *C12N 9/22* (2013.01); *C12N 15/63* (2013.01); *C12N 15/80* (2013.01); *C12N 15/81* (2013.01); *C12N 15/815* (2013.01); *C12N 15/8216* (2013.01); *C12N 15/8217* (2013.01); *C12N 15/8263* (2013.01); *C12N 15/8265* (2013.01); *C07K 14/005* (2013.01); *C07K 2319/00* (2013.01); *C12N 2510/00* (2013.01)

(58) Field of Classification Search
None
See application file for complete search history.

(56) References Cited

U.S. PATENT DOCUMENTS

| | | |
|---|---|---|
| 2006/0147978 A1 | 7/2006 | Lorens |
| 2009/0155854 A1 | 6/2009 | Yueh |
| 2014/0356958 A1 | 12/2014 | Mali |
| 2015/0064138 A1 | 3/2015 | Lu |
| 2018/0327762 A1 | 11/2018 | Maselko et al. |

FOREIGN PATENT DOCUMENTS

| | | |
|---|---|---|
| WO | WO 2015/084802 A1 | 6/2015 |
| WO | WO 2017-083501 A1 | 5/2017 |
| WO | 2018/209014 | 11/2018 |
| WO | 2020/101947 | 6/2020 |
| WO | 2021/076342 | 4/2021 |
| WO | 2021/087319 | 5/2021 |

OTHER PUBLICATIONS

Konermann et al., Genome-scale transcriptional activation by an engineered CRISPR-Cas9 complex. Nature (2015), 517: 583-588 (Year: 2015).*
Ryffel, Transgene flow: Facts, speculations and possible countermeasures. GM Crops & Food (2014), 5(4): 249-258; pp. 253-255 (Year: 2014).*
Esvelt et al., Concerning RNA-guided gene drives for the alteration of wild populations. eLife (2014) 3:e03401. DOI: 10. 7554/elife. 03401 (Year: 2014).*
Prelich, Gene Overexpression: Uses, Mechanisms, and Interpretation. Genetics (2012), 190: 841-954 (Year: 2012).*
International Patent Application No. PCT/US2016/061297, filed Nov. 10, 2016; International Preliminary Report on Patentability issued May 24, 2018; 11 pages.
International Patent Application No. PCT/US2016/061297, filed Nov. 10, 2016; International Search Report / Written Opinion issued Mar. 2, 2017; 18 pages.
Aliota, "The wMel strain of Wolbachia Reduces Transmission of Zika virus by Aedes aegypti" Jul. 2016 *Scientific Reports*, 6:28792.
Alphey, "Sterile-Insect Methods for Control of Mosquito-Borne Diseases—An Analysis" Apr. 2011 *Vector Borne Zoonotic Dis.*, 10(3):295-311.
Annaluru, "Total Synthesis of a Functional Designer Eukaryotic Chromosome" Apr. 2014 *Science*, 344(6179):55-8.
Bai, "Homology-integrated CRISPR-Cas (HI-CRISPR) system for one-step multigene disruption in *Saccharomyces cerevisiae*" 2014 *ACS Synth Biol* 4(5):585-594, First author last name is Bao.

(Continued)

*Primary Examiner* — Abigail Vanhorn
*Assistant Examiner* — Catherine Konopka
(74) *Attorney, Agent, or Firm* — Mueting Raasch Group

(57) ABSTRACT

This disclosure describes, in one aspect, a cell that includes a biocontainment system. Generally, the biocontainment system includes a coding region whose overexpression decreases growth of the cell, a transcription regulatory region that includes a silent mutation and is operably linked upstream of the coding region, and a polynucleotide that encodes a programmable transcription activator engineered to bind to the transcription regulatory region in the absence of the silent mutation. Thus, in the absence of the silent mutation, the programmable transcription activator induces overexpression of the coding region; in the presence of the silent mutation, the programmable transcription activator does not initiate overexpression of the coding region.

24 Claims, 7 Drawing Sheets

Specification includes a Sequence Listing.

(56) References Cited

OTHER PUBLICATIONS

Baryshnikova, "Quantitative analysis of fitness and genetic interactions in yeast on a genome scale" 2010 *Nat. Methods*, 7:1017-1024.

Bikard, "Programmable repression and activation of bacterial gene expression using an engineered CRISPR-Cas system" Aug. 2013 *Nucleic Acids Res.*, 41(15):7429-37.

Black, "Why RIDL is not SIT" Aug. 2011 *Trends Parasitol.*, 27(8):362-70.

Boeke, Genome Engineering. The Genome Project-Write. *Science* 353, 126-7 (2016).

Boete, "Impact of mating behaviour on the success of malaria control through a single inundative release of transgenic mosquitoes" Apr. 2014 *J Theor Biol.*, 347:33-43.

Burgos, "The impact of herbicide-resistant rice technology on phenotypic diversity and population structure of United States weedy rice" 2014 *Plant Physiol.* 166, 1208-20.

Chappell, "A renaissance in RNA synthetic biology: new mechanisms, applications and tools for the future" Jun. 2015 epub *Curr Opin Chem Biol.*, 28:47-56.

Chavez, "Comparison of Cas9 activators in multiple species" Jul. 2016 *Nat Methods*, 13(7):563-567.

Chen, "Naturally Occurring Incompatibilities between Different Culex pipiens pallens Populations as the Basis of Potential Mosquito Control Measures" 2013 *PLoS Negl Trop Dis.*, 7(1):e2030.

Cherry, "*Saccharomyces* Genome Database: the genomics resource of budding yeast" 2012 *Nucleic Acids Res.*, 40(Database issue):D700-705.

Davis, "Engineered Underdominance Allows Efficient and Economical Introgression of Traits into Pest Populations" Sep. 2001 *J Theor Biol.*, 212(1):83-98.

Dicarlo, "Genome engineering in *Saccharomyces cerevisiae* using CRISPR-Cas systems" epub Mar. 2013 *Nucleic Acids Res.*, 41(7):4336-43.

Dodson, "Wolbachia Enhances West Nile Virus (WNV) Infection in the Mosquito Culex tarsalis" Jul. 2014 *PLoS Negl Trop Dis.*, 8(7):e2965.

Drubin, "Yeast actin-binding proteins: evidence for a role in morphogenesis" 1988 *J Cell Biol.*, 107(6):2551-2561.

Engler, "A golden gate modular cloning toolbox for plants" 2014 *ACS Synth Biol.*, 3(11):839-843.

Esvelt, "Orthogonal Cas9 proteins for RNA-guided gene regulation and editing" 2013 *Nat Methods*, 10(11):1116-1121.

Evdokimov, "Structural basis for the fast maturation of Arthropoda green fluorescent protein" 2006 *EMBO Rep.* 7:1006-12.

Ewen-Campen, "Optimized strategy for in vivo Cas9-activation in *Drosophila*" Aug. 2017 *PNAS*, 114 (35):9409-9414.

Fernando, "Molecular circuits for associative learning in single-celled organisms" Oct. 2008 epub *J R Soc Interface*, 6;6(34):463-9.

Gallagher, "Multilayered genetic safeguards limit growth of microorganisms to defined environments" online Jan. 2015 *Nucleic Acids Res.*, 43(3): 1945-1954.

Gallwitz, "Molecular cloning of the actin gene from yeast *Saccharomyces cerevisiae*" 1980 *Nucleic Acids Res.*, 8(5):1043-1059.

Gao, "Comparison of TALE designer transcription factors and the CRISPR-dCas9 in regulation of gene expression by targeting enhancers" Nov. 2014 *Nucleic Acids Res.*, 42(20):e155.

Geng, "Forms Distinct Complexes with the Ypt1 Rab GTPase and the Reticulon Rtnlp" 2005 *Eukaryot Cell*, 4(7):1166-1174.

Gietz, "Yeast transformation by the LiAc/SS Carrier DNA/PEG method" 2006 *Methods Mol. Biol.*, 313:107-120.

Gressel, "Dealing with transgene flow of crop protection traits from crops to their relatives" May 2014 *Pest Mgmt. Sci.*, 10 pgs. DOI 10.01008/ps.8350.

Grether, "The head involution defective gene of *Drosophila melanogaster* functions in programmed cell death" Jul. 1995 *Genes Dev.*, 9(14):1694-708.

Guillier, "Automated image analysis of bacterial colony growth as a tool to study individual lag time distributions of immobilized cells" 2006 *J. Microbiol. Methods*, 65:324-334.

Harris, "Field performance of engineered male mosquito" Oct. 2011 *Nat Biotechnol.*, 29(11):1034-7.

Heinrich, "A repressible female-specific lethal genetic system for making transgenic insect strains suitable for a sterile-release program" Jul. 2000 *Proc Natl Acad Sci U S A.*, 97(15): 8229-8232.

Hsieh (not Nathans as cited in bibliog.), "A new secreted protein that binds to Wnt proteins and inhibits their activites" 1999 *Nature* 398:431-436.

Husken, "Evaluating biological containment strategies for pollen-mediated gene flow" Apr.-Jun. 2010 *Environ Biosafety Res.*, 9(2):67-73.

Jia, "Next-generation CRISPR-Cas9 transcriptional activation in using flySAM" May 2018 *Proc Natl Acad Sci U S A*, 115(18):4719-4724.

Kalyna, "Ectopic Expression of atRSZ33 Reveals Its Function in Splicing and Causes Pleiotropic Changes in Development" Sep. 2003 *Mol Biol Cell*, 14(9):3565-3577.

Kaneda, "The transcription factor OsNAC4 is a key positive regulator of plant hypersensitive cell death" Apr. 2009 *EMBO J.*, 28(7):926-36.

Kiani, "Cas9 gRNA engineering for genome editing, activation and repression" Sep. 2015 *Nat Methods*, epub, 12(11):1051-4.

Kim, "Overexpression of wound responsive RNA binding proteins induces leaf senescence and hypersensitive like cell death" 2008 *New Phytol.*, 180(1):57-70.

Konermann, "Genome-scale transcriptional activation by an engineered CRISPR-Cas9 complex" Jan. 2015 *Nature*, 517(7536):583-8.

Lajoie, "Genomicalfy Recoded Organisms Expand Biological Functions" Oct. 2013 *Science*, 342(6156): 357-360.

Lin, "In Vivo Transcriptional Activation Using CRISPR-Cas9 in *Drosophila* Improving containment strategies in biopharming" Oct. 2015 *Genetics*, 201:433-442.

Liu, "Construction of a Gal1-Regulated Yeast Cdna Expression Library and Its Application to the Identification of Genes Whose Overexpression Causes Lethality in Yeast" 1992 *Genetics* 132(3):665-673.

Lowder, "A CRSPR-Cas9 Toolbox for Multiplexed Plant Genome Editing and Transcriptional Regulation" Oct. 2015 *Plant Physiol.*, 169(2):971-85.

Luo, "GM gene deletor fused loxP FRT recognition sequences dramatically improve the efficiency of FLP or CRE recombinase on transgene excision from pollen and seed of tobacco plants" Mar. 2007 *Plant Biotechnol J.*, 5(2):263-274.

Marshall, "Confinement of gene drive systems to local populations—A comparative analysis" Feb. 2012 *J Theor Biol.*, 294:153-71.

Maselko, "Engineering species-like barriers to sexual reproduction" Oct. 2017 *Nat Commun.*, 8(1):883.

Maselko, "Genetic incompatibility combined with female-lethality is effective and robust in simulations of Aedes aegypti population control" Preprint May 2018; DOI: 10.1101/316406.

Moreno, "Design and Construction of Synthetic Species" Jul. 2012 *PLOS one*, 7(7): e39054.

Murphy, "Improving containment strategies in biopharming" Sep. 2007 *Plant Biotechnol J.*, 5(5):555-69.

Nash, "Isolation and characterization of WHI3, a size-control gene of *Saccharomyces cerevisiae*" 2001 *Genetics* 157(4):1469-1480.

Neff, "Isolation of the β-tubulin gene from yeast and demonstration of its essential function in vivo" 1983 *Cell* 33(1):211-219.

Otte, "Erv41p and Erv46p: New Components of COPII Vesicles Involved in Transport between the ER and Golgi Complex" 2001 *J Cell Biol.*, 152(3):503-518.

Oye, "Biotechnology. Regulating gene drives" 2014 *Science*, 345:626-8.

Reeves, "First Steps towards Underdominant Genetic Transformation of Insect Populations" May 2014 *PLoS One*, 9(5):e97557.

Richardson, "Enhancing homology-directed genome editing by catalytically active and inactive CRISPR-Cas9 using asymmetric donor DNA" 2016 *Nat. Biotechnol.* 34, 339-344.

(56) References Cited

OTHER PUBLICATIONS

Robert, "A Reduce and Replace Strategy for Suppressing Vector-Borne Diseases—Insights from a Deterministic Model" Sep. 2013 *PLoS One*, 8(9):e73233.
Rorth, "A modular misexpression screen in *Drosophila* detecting tissue-specific phenotype" 1996 Proceedings of the National Academy of Sciences of the United States of America, 93(22):12418-12422.
Röther, "Swt1, a Novel Yeast Protein, Functions in Transcription" 2006 *J Biol Chem.*, 281(48):36518-36525.
Rovner, "Recoded organisms engineered to depend on synthetic amino acids" Feb. 2015 *Nature*, 518(7537):89-93.
Skružný, "An Endoribonuclease Functionally Linked to Perinuclear mRNP Quality Control Associates with the Nuclear Pore Complexes" 2009 *PLoS Biol.*, 7(1):e1000008.
Sopko, "Mapping pathways and phenotypes by systematic gene overexpression" 2006 *Mol Cell*, 21(3):319-330.
Storici, "Delitto perfetto targeted mutagenesis in yeast with oligonucleotides" 2003 *Genet Eng* 25:189-207.
Teixeira, "The YEASTRACT database: an upgraded information system for the analysis of gene and genomic transcription regulation in *Saccharomyces cerevisiae*" 2014 *Nucleic Acids Res.*, 42:D161-6.
Thomas, "Insect Population Control Using a Dominant, Repressible, Lethal Genetic System" Mar. 2000 *Science*, 287(5462):2474-2476.
Turelli, "Theory and speciation" 2001 *Trends in Ecology and Evolution*, 16:330-343.
Van Dijken, "An interlaboratory comparison of physiological and genetic properties of four *Saccharomyces cerevisiae* strains" 2000 *Enzyme Microb. Technol.*, 26:706-714.
Waters, "Rationally-engineered reproductive barriers using CRISPR & CRISPRa—an evaluation of the synthetic species concept in *Drosophila melanogaster*" Feb. 2018 Preprint: doi: https://doi.org/10.1101/259010.
Wright, "Characterization of COX9, the nuclear gene encoding the yeast mitochondrial protein cytochrome c oxidase subunit VIIa. Subunit VIIa lacks a leader peptide and is an essential component of the holoenzyme" 1986 *J Biol Chem.*, 261(36):17183-17191.
Yoshida, "Superwoman1 cleistogamy a hopeful allele for gene containment in GM rice" Nov. 2007 *Plant Biotechnol J.*, 5(6):835-46.
Zabalou, "Wolbachia-induced cytoplasmic incompatibility as a means for insect pest population control" Oct. 2004 *PNAS*, 101(42):15042-15045.
Zalatan, "Engineering Complex Synthetic Transcriptional Programs with CRISPR RNA Scaffolds" Jan. 2015 *Cell*, 160(1-2):339-50.
Zhang, "Mapping of transcription start sites in *Saccharomyces cerevisiae* using 5' SAGE" 2005 *Nucleic Acids Res.*, 33:2838-51.
International Patent Application No. PCT/US2020/058301, filed Oct. 31, 2019; International Preliminary Report on Patentability issued Feb. 22, 2021; 9 pages.
Akbari et al., Biosafety. Safeguarding gene drive experiments in the laboratory. Science 349, 927-929 (2015).
Aliota et al., The wMel strain of Wolbachia Reduces Transmission of Zika virus by Aedes aegypti. Scientific Reports, 6:28792 (2016).
Alphey et al., Genetic control of Aedes mosquitoes. Pathog Glob Health 107, 170-179 (2013).
Alphey et al., Malaria control with genetically manipulated insect vectors. Science 298, 119-121 (2002).
Alphey, Genetic control of mosquitoes. Annu Rev Entomol 59, 205-224 (2014).
Bajer et al. Partial migration to seasonally-unstable habitat facilitates biological invasions in a predator-dominated system. Oikos, 124: 1520-1526 (2015).
Bank et al., The limits to parapatric speciation: Dobzhansky-Muller incompatibilities in a continent-island model. Genetics 191, 845-863 (2012).
Beckmann et al., A Wolbachia deubiquitylating enzyme induces cytoplasmic incompatibility. Nat Microbiol 2, 17007 (2017).
Buchman et al., Site-specific transgenesis of the *Drosophila melanogaster* Y-chromosome using CRISPR/Cas9. Insect Mol Biol 28, 65-73 (2019).
Bull et al., The gene drive bubble: New realities. PLoS Genet 13, e1006850 (2017).
Caceres, Mass rearing of temperature sensitive genetic sexing strains in the Mediterranean fruit fly (*Ceratitis capitata*). Genetica 116, 107-116 (2002).
Carvalho et al., Mass production of genetically modified Aedes aegypti for field releases in Brazil. J Vis Exp, e3579 (2014).
Champer et al., Cheating evolution: engineering gene drives to manipulate the fate of wild populations. Nat Rev Genet 17, 146-159 (2016).
Champer et al., Novel CRISPR/Cas9 gene drive constructs reveal insights into mechanisms of resistance allele formation and drive efficiency in genetically diverse populations. PLoS Genet 13, e1006796 (2017).
Concha et al., A transgenic male-only strain of the New World screwworm for an improved control program using the sterile insect technique. BMC Biol 14, 72 (2016).
Condon et al. Genetic sexing through the use of Y-linked transgenes. Insect Biochem Mol Biol. Nov. 2007;37(11):1168-76.
Deliberto et al., "Hybrid Rice Production Costs and Returns: Comparisons with conventional clearfield varieties," 2010, LSU AgCenter Staff Rep., 1-8.
Dobzhansky, Studies on Hybrid Sterility. II. Localization of Sterility Factors in *Drosophila pseudoobscura* Hybrids. Genetics 21, 113-135 (1936).
Dominiak et al., Evaluating irradiation dose for sterility induction and quality control of mass-produced fruit fly *Bactrocera tryoni* (Diptera: Tephritidae). J Econ Entomol 107, 1172-1178 (2014).
Dong et al. Synthetic CRISPR-Cas gene activators for transcriptional reprogramming in bacteria. Nat Commun 9, 2489 (2018).
Dye, Models for the Population Dynamics of the Yellow Fever Mosquito, Aedes Aegypti, Journal of Animal Ecology 53(1):247-268 (1984).
Facchinelli et al., Field cage studies and progressive evaluation of genetically-engineered mosquitoes. PLoS Negl Trop Dis 7, e2001 (2013).
Fu et al., Female-specific flightless phenotype for mosquito control. Proc Natl Acad Sci U S A 107, 4550-4554 (2010).
Galizi et al., A synthetic sex ratio distortion system for the control of the human malaria mosquito. Nat Commun 5, 3977 (2014).
Gantz et al., Genome editing. The mutagenic chain reaction: a method for converting heterozygous to homozygous mutations. Science 348, 442-444 (2015).
Gantz et al., Highly efficient Cas9-mediated gene drive for population modification of the malaria vector mosquito *Anopheles stephensi*. Proc Natl Acad Sci U S A 112, E6736-6743 (2015).
Geng et al., *Saccharomyces cerevisiae* Rab-GDI displacement factor ortholog Yip3p forms distinct complexes with the Ypt1 Rab GTPase and the reticulon Rtn1p. Eukaryot Cell 4, 1166-1174 (2005).
Goindin et al., Parity and longevity of Aedes aegypti according to temperatures in controlled conditions and consequences on dengue transmission risks. PLoS One 10, e0135489 (2015).
Gutierrez et al., A model describing the effect of sex-reversed YY fish in an established wild population: The use of a Trojan Y chromosome to cause extinction of an introduced exotic species. J Theor Biol 241, 333-341 (2006).
Hammond et al., A CRISPR-Cas9 gene drive system targeting female reproduction in the malaria mosquito vector *Anopheles gambiae*. Nat Biotechnol 34, 78-83 (2016).
Hammond et al., The creation and selection of mutations resistant to a gene drive over multiple generations in the malaria mosquito. PLoS Genet 13, e1007039 (2017).
Harris et al., Successful suppression of a field mosquito population by sustained release of engineered male mosquitoes. Nat Biotechnol 30, 828-830 (2012).
Harvey-Samuel et al., Pest control and resistance management through release of insects carrying a male-selecting transgene. BMC Biol 13, 49 (2015).

(56) References Cited

OTHER PUBLICATIONS

Harvey-Samuel et al., Towards the genetic control of invasive species. Biol Invasions 19, 1683-1703 (2017).
Hendrichs, et al., Medfly Areawide Sterile Insect Technique Programmes for Prevention, Suppression or Eradication: the Importance of Mating Behavior Studies, 85 (1), 1-13 223 (2002).
Jin et al., Engineered female-specific lethality for control of pest Lepidoptera. ACS Synth Biol 2, 160-166 (2013).
Kandul et al. Transforming Insect population control with precision guided sterile males with demonstration in flies. Nat Commun 10, 84 (2019).
Kraemer et al., The global distribution of the arbovirus vectors Aedes aegypti and Ae. albopictus. Elife 4, e08347 (2015).
Legros et al., Evaluation of location-specific predictions by a detailed simulation model of Aedes aegypti populations. PLoS One 6, e22701 (2011).
Li et al., CRISPR/Cas9-mediated mutagenesis of the white and Sex lethal loci in the invasive pest, *Drosophila suzukii*. Biochem Biophys Res Commun 469, 911-916 (2016).
Li et al., Transgenic sexing system for genetic control of the Australian sheep blow fly *Lucilia cuprina*. Insect Biochem Mol Biol 51, 80-88 (2014).
Magori et al., Skeeter Buster: a stochastic, spatially explicit modeling tool for studying Aedes aegypti population replacement and population suppression strategies. PLoS Negl Trop Dis 3, e508 (2009).
Marshall et al., Overcoming evolved resistance to population-suppressing homing-based gene drives. Sci Rep 7, 3776 (2017).
Mohanty et al., Wolbachia: A biological control strategy against arboviral diseases. J Vector Borne Dis 53, 199-207 (2016).
Navarro, Gene drive in *Drosophilamelanogaster* and Aedes aegypti. Doctoral thesis (online). Cardiff Univeristy. Sep. 2017 [retrieved on Jan. 4, 2021].
Noble et al. Current CRISPR gene drive systems are likely to be highly invasive in wild populations. bioRxiv 219022 (2017).
Novitski et al., The entire compound autosomes of *Drosophila melanogaster*. Genetics 98, 257-273 (1981).
Orr et al., The evolution of postzygotic isolation: accumulating Dobzhansky-Muller incompatibilities. Evolution 55, 1085-1094 (2001).
Pfeiffer et al., Refinement of tools for targeted gene expression in *Drosophila*. Genetics 186, 735-755 (2010).
Pfeiffer et al., Using translational enhancers to increase transgene expression in *Drosophila*. Proc Natl Acad Sci U S A 109, 6626-6631 (2012).
Piatek et al., Targeted genome regulation via synthetic programmable transcriptional regulators. Crit Rev Biotechnol 37, 429-440 (2017).
Presgraves, The molecular evolutionary basis of species formation. Nat Rev Genet 11, 175-180 (2010).
Rendon et al., Medfly (Diptera: Tephritidae) genetic sexing: large-scale field comparison of males-only and bisexual sterile fly releases in Guatemala. J Econ Entomol 97, 1547-1553 (2004).
Schetelig et al., Site-specific recombination for the modification of transgenic strains of the Mediterranean fruit fly *Ceratitis capitata*. Proc Natl Acad Sci U S A 106, 18171-18176 (2009).
Shalem et al., High-throughput functional genomics using CRISPR-Cas9. Nat Rev Genet 16, 299-311 (2015).
Sheppard et al. The Dynamics of an Adult Population of Aedes aegypti in Relation to Dengue Haemorrhagic Fever in Bangkok. J. Anim. Ecol. 38, 661-702 (1969).
Shockett et al., A modified tetracycline-regulated system provides autoregulatory, inducible gene expression in cultured cells and transgenic mice. Proc Natl Acad Sci U S A 92, 6522-6526 (1995).
Sinkins et al., Gene drive systems for insect disease vectors. Nat Rev Genet 7, 427-435 (2006).
Smanski et al., Genetic manipulation of sex ratio in mammals: the Reaper comes for Mickey. EMBO Rep 20, e48577 (2019).
Tan et al., Transgene-based, female-specific lethality system for genetic sexing of the silkworm, *Bombyx mori*. Proc Natl Acad Sci U S A 110, 6766-6770 (2013).
Thailayil et al., Spermless males elicit large-scale female responses to mating in the malaria mosquito *Anopheles gambiae*. Proc Natl Acad Sci U S A 108, 13677-13681 (2011).
Thresher et al. Sex-ratio-biasing constructs for the control of invasive lower vertebrates. Nat. Biotechnol. 32, 424-427 (2014).
Van Dijken et al., *Arabidopsis trehalose*-6-phospate synthase 1 is essential for normal vegetative growth and transition in flowering, Plant physiology 135.2 (2004): 969-977.
Vargas-Teran et al., Impact of Screwworm Eradication Programmes Using the Stirele Insect Technique. pp. 949-978 published in Sterile insect technique: principles and practice in area-wide integrated pest management (Dyck et al (eds.)). Dec. 2020. (31 pages).
Wise De Valdez et al., Genetic elimination of dengue vector mosquitoes. Proc Natl Acad Sci U S A 108, 4772-4775 (2011).
Wyss, Screwworm eradication in the Americas. Ann N Y Acad Sci 916, 186-193 (2000).
Yan et al., Building early-larval sexing systems for genetic control of the Australian sheep blow fly *Lucilia cuprina* using two constitutive promoters. Sci Rep 7, 2538 (2017).
International Patent Application No. PCT/US2018/031950, filed May 10, 2018; International Preliminary Report on Patentability issued Nov. 12, 2019; 7 pages.
International Patent Application No. PCT/US2018/031950, filed May 10, 2018; International Search Report / Written Opinion issued Jul. 23, 2018; 11 pages.
International Patent Application No. PCT/US2019/059826, filed Nov. 5, 2019; International Preliminary Report on Patentability issued May 11, 2021; 6 pages.
International Patent Application No. PCT/US2019/059826, filed Nov. 5, 2019; International Search Report / Written Opinion mailed May 21, 2020; 9 pages.
International Patent Application No. PCT/US2020/053749, filed Oct. 1, 2020; International Search Report / Written Opinion mailed Jul. 23, 2021; 14 pages.
International Patent Application No. PCT/US2020/058301, filed Oct. 30, 2020; International Search Report / Written Opinion mailed Feb. 22, 2021; 10 pages.
Ryffel, Transgene flow: Facts, speculations and possible countermeasures. GM Crops & Food (2014), 5(4): 249-258 (Year: 2014).
Prelich, Gene Overexpression: Uses, Mechanisms, and Interpretation. Genetics (2012), 190: 841-854 (Year: 2012).
Wong et al., Production of reproductively sterile fish: A mini-review of germ cell elimination technologies. General and Comparative Endocrinology (2015), 221: 3-8 (Year: 2015).
Breyer et al., Biosafety considerations associated with molecular farming in genetically modified plants Journal of Medicinal Plants Research (2009), 3(11): 825-838. (Year: 2009).
Stuurman et al., Ectopic overexpression of *Drosophila lamin* C is stage-specific lethal. Experimental Cell Research (1999) 248(2):350-357 (Year: 1999).
Leclere and Bartel. A library of *Arabidopsis* 35S-cDNA lines for identifying novel mutants. Plant Molecular Biology (2001) 46: 695-703 (Year: 2001).
Wodarz, Molecular control of cell polarity and asymmetric cell division in *Drosophila neuroblasts*. Current Opinion in Cell Biology (2005) 17(5): 475-481 (Year: 2005).

* cited by examiner

BIOCONTAINMENT/BIOCONTROL SYSTEM AND METHODS

CROSS-REFERENCE TO RELATED APPLICATION

This application is a continuation application of U.S. patent application Ser. No. 15/775,164, filed May 10, 2018, which is the § 371 U.S. National Stage of International Application No. PCT/US2016/061297, filed 10 Nov. 2016, which claims priority to U.S. Provisional Patent Application No. 62/253,954, filed Nov. 11, 2015, each of which is incorporated herein by reference in its entirety.

GOVERNMENT FUNDING

This invention was made with government support under 58-3640-1-734, 59-0206-4-019, 59-0206-9-070, 59-0790-4-091 awarded by Agricultural Research Service, USDA. The government has certain rights in the invention.

This invention was made with government support under 2006-55606-16629 awarded by the National Institute of Food and Agriculture, USDA. The government has certain rights in the invention."

SEQUENCE LISTING

This application contains a Sequence Listing electronically submitted to the United States Patent and Trademark Office via Patent Center as an XML file entitled "0110-000482US02" having a size of 56,473 bytes and created on November 19 2023. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

SUMMARY

This disclosure describes, in one aspect, a cell that includes a biocontainment system. Generally, the biocontainment system includes a coding region whose overexpression decreases growth of the cell, a transcription regulatory region that includes a silent mutation and is operably linked upstream of the coding region, and a polynucleotide that encodes a programmable transcription activator engineered to bind to the transcription regulatory region in the absence of the silent mutation. Thus, in the absence of the silent mutation, the programmable transcription activator induces overexpression of the coding region; in the presence of the silent mutation, the programmable transcription activator does not initiate overexpression of the coding region.

Accordingly, an organism that is homozygous for the biocontainment system grows normally. In contrast, an organism that becomes heterozygous for the biocontainment system—whether as a result of sexual reproduction with another variety of the organism or by some spontaneous genetic event—exhibits retarded growth and/or death so that any hybrids can be efficiently culled from the population.

In some embodiments, the cell can be a single-celled organism. In other embodiments, the cell can be a germ cell of a multicellular organism.

In some embodiments, the programmable transcription activator can include dCas9 fused to an activation domain.

In some embodiments, the coding region can encode a cytoskeletal polypeptide, an ER-Golgi vesicle polypeptide, an mRNA processing polypeptide, an electron transport polypeptide, a nuclear trafficking polypeptide, a chromosome segregation polypeptide, a spindle pole duplication polypeptide, or an oxidative stress polypeptide.

In some embodiments, overexpression of the coding region can be lethal to the cell.

In some embodiments, the cell can include a second biocontainment system.

In another aspect, this disclosure describes a method of limiting hybridization of a genetically-modified organism with a genetically dissimilar variant. Generally, the method includes providing an organism genetically modified to include any embodiment of the biocontainment system summarized above so that a cross between the genetically-modified organism and the genetically dissimilar variant organism results in progeny that exhibit a phenotype that is distinct from the genetically-modified organism.

In some embodiments, the genetically dissimilar variant can include a wild-type organism. In other embodiments, the genetically dissimilar variants can include a different genetic modification compared to the genetically-modified organism having the biocontainment system.

In some embodiments, the phenotype exhibited by the progeny can include lethality.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
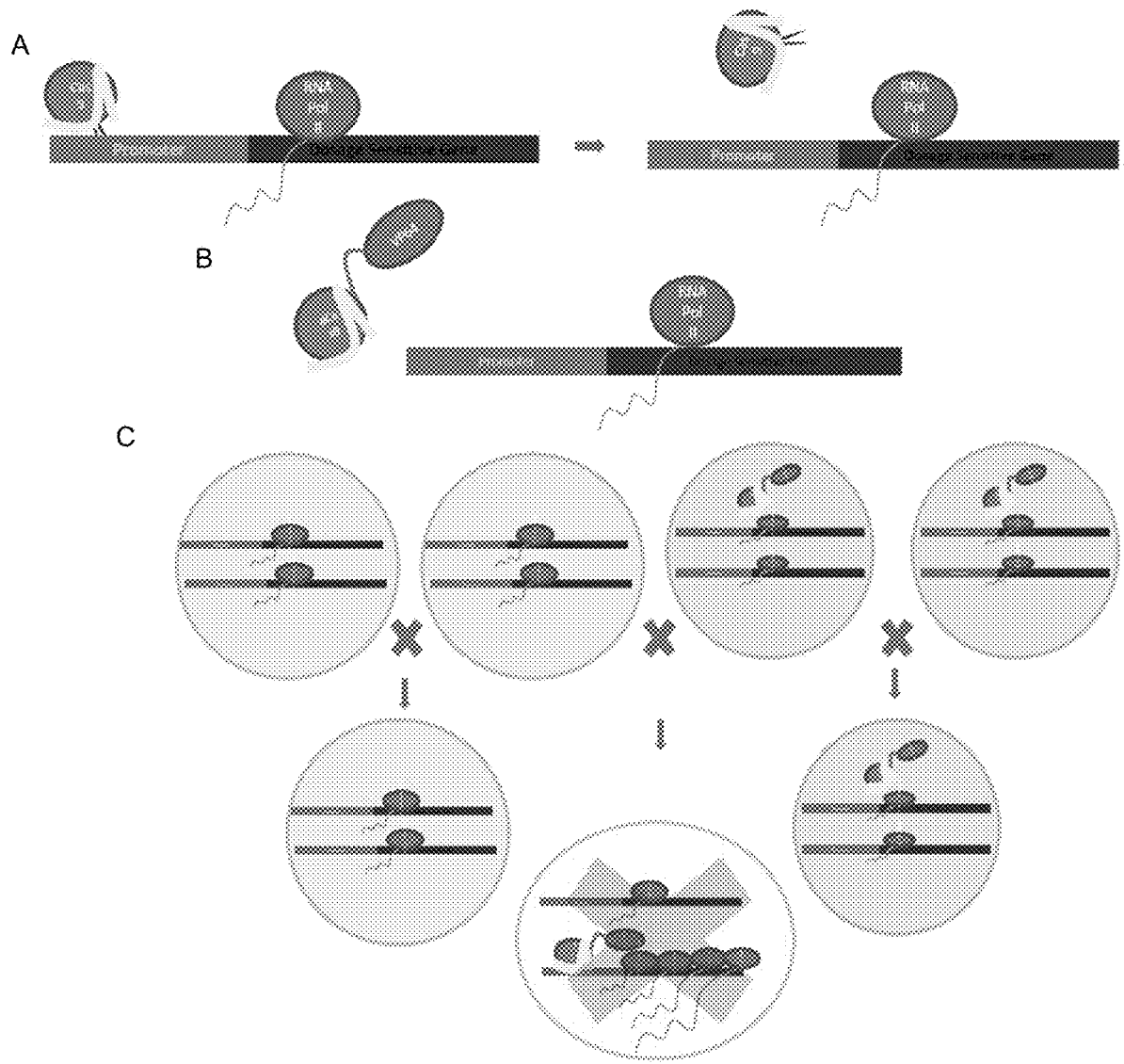
FIG. 1. Schematic diagram showing a general overview of synthetic incompatibility. (A) Silent mutations are introduced upstream of expression-sensitive coding regions. (B) A transcriptional activator is engineered to bind to the parental wild-type sequence. (C) A cross between a wild-type organism (one that contains the parental promoter sequence) and an organism engineered as shown in (A) and (B) will result in overexpression of the parental allele.

This disclosure describes a biocontainment/biocontrol system, cells and organisms that include such systems, and methods involving the construction and use of such systems. As used herein, the term "biocontainment/biocontrol system" and variations thereof refer to a genetic system that decreases the likelihood and/or extent to which a genetically-modified organism can sexually reproduce with a genetically dissimilar variant-whether wild-type or genetically modified in another way. In use, the system can decrease the likelihood and/or extent to which a genetic modification in, for example, a genetically-modified crop variety can spread into other variants. The system also can decrease the likelihood and/or extent to which a genetic modification can be diluted in a genetically-modified variety by the re-introduction of a wild-type genotype into a population of the genetically-modified variety.

Genetic recombination due to sexual reproduction is a source of tremendous genetic variation and provides a mechanism for generating organisms with novel combinations of traits. Humans have exploited this process, often unknowingly, for the domestication of plants and animals. Unwanted genetic recombination also takes place between domesticated and wild varieties of plants and animals. This is of particular concern in agricultural systems where seed production or Organic (non-GMO) certification is concerned since unwanted crosses diminish the value of a crop. Farmers usually prevent conflicts via spatial and temporal separation which often requires co-ordination with neighboring farms.

More recently, synthetic biology applications in which plants are engineered to make pharmaceuticals or other industrial compounds require effective biocontainment strategies in order to prevent contamination of the food supply. Determining sufficient spatial separation necessary for such protection is complicated and considers factors such as, for example, pollen size, duration of pollen viability, the presence of wild relatives, and typical meteorological conditions. For example, as of 2015 the U.S. Animal and Plant Health Inspection Service (APHIS), which regulates the environmental release of genetically modified plants, requires that corn engineered for the production of pharmaceutical or industrial compounds must be separated from all other corn by at least 1 mile despite 0.25 mile being sufficient to achieve 99.9% purity. This creates a substantial burden for companies wishing to use plant-based production systems.

Biocontainment approaches other than physical separation have been investigated, but each has at least one major drawback that prevents wide-spread adoption. Cleistogamy, in which flowers never open and therefore must self-pollinate is not applicable to all species. Maternal inheritance of transgenes by plastid engineering is likewise not applicable to all species and pollen-mediated transfer of plastids at low frequencies may be common in many other species. Excising a transgene from a pollen-expressed recombinase may be highly efficient, but control of recombinase activity can interfere with normal propagation. Total sterility requires asexual propagation and is not practical for many species. Using exogenous chemical inputs to regulate lethal genes requires changes to normal cultivation techniques and genome reprogramming to confer dependence on synthetic compounds. Furthermore, with the exceptions of cleistogamy and asexual propagation, these methods only prevent outward gene-flow. Unwanted flow of genes into genetically engineered plants, however, can result in bioncontainment failure in subsequent generations.

Figure 2:
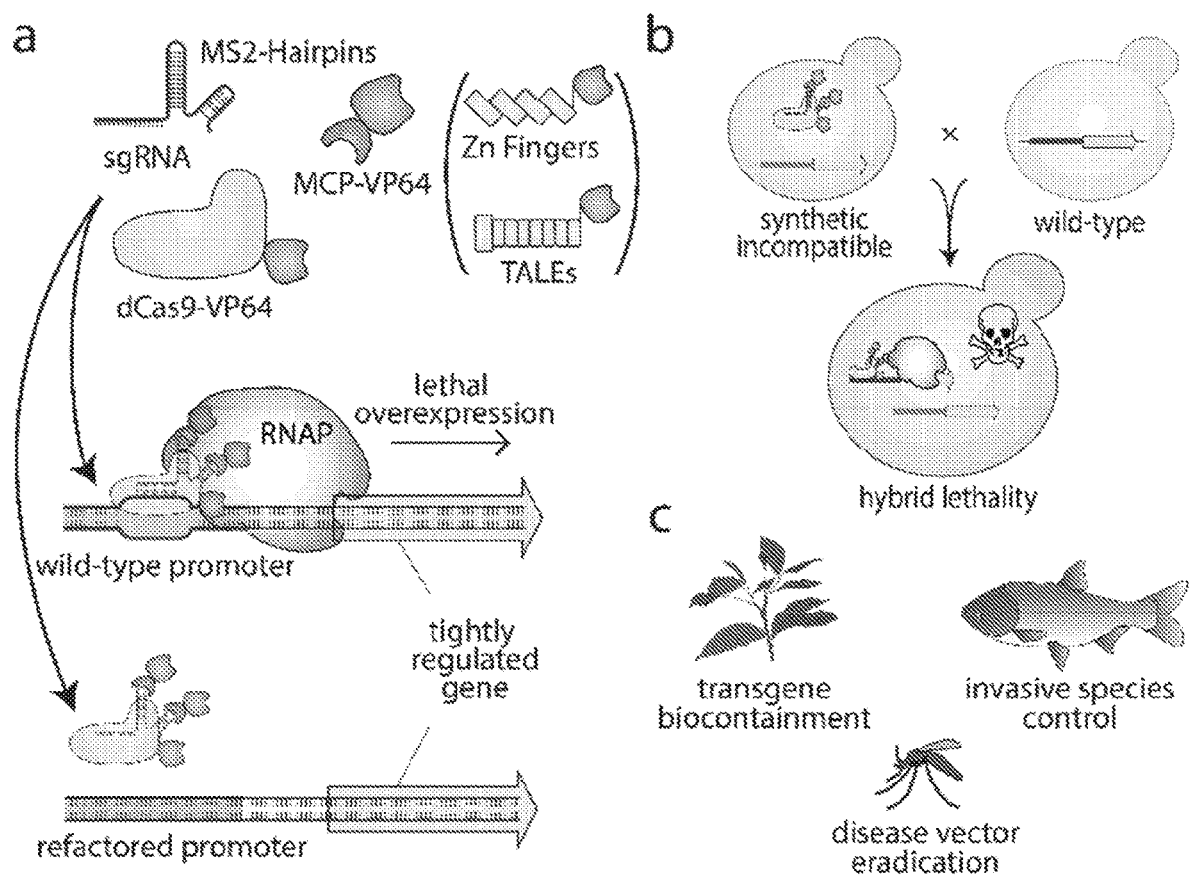
FIG. 2. Schematic diagram showing illustrating synthetic incompatibility in detail. (A) Macromolecular components that constitute programmable transcription factors (above), and schematic illustration showing lethal expression from a wild-type promoter but not a refactored promoter (below). (B) Illustration of hybrid lethality upon mating of wild-type (right cell) and SI (left cell) parents. Macromolecular components are labeled in (A), dark DNA signifies WT promoter, and light DNA signifies refactored promoter. Skull and crossbones indicates a non-viable genotype as lethal expression is initiated from the wild-type promoter. (C) Possible applications for engineered speciation.

This disclosure describes a novel biocontainment approach in which a programmable transcriptional activator (e.g., dCas9-VP64) monitors for the presence of a binding site upstream of an expression-sensitive coding region—i.e., any portion of the genome whose overexpression results in death or a severely deleterious phenotype. Thus, overexpression of an expression-sensitive coding region can reduce the reproductive fitness of the organism in which the expression-sensitive coding region is overexpressed and, in certain embodiments, even prevent the organism from reproducing. The upstream binding site is mutated in the engineered organism (FIG. 1A and FIG. 2A) that express the transcriptional activator (FIG. 1B and FIG. 2A). The mutation in the upstream binding site negates binding of the programmable transcription activator so that expression of the coding region is at a normal, nonlethal level.

Sexual crossing with the wild-type organisms activates the system (FIG. 1C and FIG. 2B). The programmable transcription activator is able to bind to the non-mutated, wild-type upstream binding site contributed by the wild-type parent, causing the lethal overexpression of the expression-sensitive gene. The engineered strain can effectively be considered a distinct species from the wild-type since it is no longer sexually compatible with the wild-type. This synthetic incompatibility approach does not require any changes in culture techniques or additional chemical inputs to maintain biocontainment. Furthermore, multiple orthogonal circuits can be introduced so that the same basic strategy can be used simultaneously in the same organismal background.

Beyond transgene containment, synthetic incompatibility also can be used for biological insect control via an alternative to the widespread sterile insect technique (SIT). SIT involves the release of sterile male insects (e.g., mosquitoes) which then find females to mate with. This can be an effective control strategy since the females of many insects often mate only once per lifetime or clutch of eggs. A drawback to SIT is that the males are typically sterilized via irradiation, which can cause behavioral changes that make them significantly less successful at finding a mate than non-irradiated males. Therefore, many more irradiated males have to be released for successful population control. Another drawback is that this technique is not applicable to several important insect species since the dose necessary for sterilization is not sufficiently below the lethal dose. Synthetic incompatibility is an appealing alternative since it requires no irradiation. Thus, synthetic incompatibility can produce more competitive males and may be applied to a larger number of insects.

The utility of synthetic incompatibility was established in the model organism *Saccharomyces cerevisiae* since it is easy to genetically manipulate, can be propagated as either a haploid or diploid, and has similar molecular biology to higher organisms. The approach involved first identify genes that can be sufficiently overexpressed by the programmable transcription factor dCas9-VP64 to cause a strong defect in growth.

Six target genes (Table 1) were initially chosen to be targeted for overexpression based on an "inviable" phenotype reported in the *Saccharomyces* Genome Database. Transcriptional start sites (TSS) were retrieved using the IGV genome browser (Broad Institute, Cambridge, MA) and previously mapped start sites. sgRNAs were designed to bind unique sequences upstream of NGG protospacer adjacent motif (PAM) sites in an approximately 250 bp window upstream of predicted transcriptional start sites of candidate coding regions. Four target sites were selected for each gene.

TABLE 1

S. cerevisiae overexpression target genes

| Gene | Core Function |
| --- | --- |
| TUB2 | Cytoskeletal |
| ACT1 | Cytoskeletal |
| ABP1 | Regulation of actin cytoskeleton |
| YIP3 | ER-Golgi vesicle transport |
| SWT1 | mRNA quality control |
| COX1 | Electron transport chain |

Figure 3:
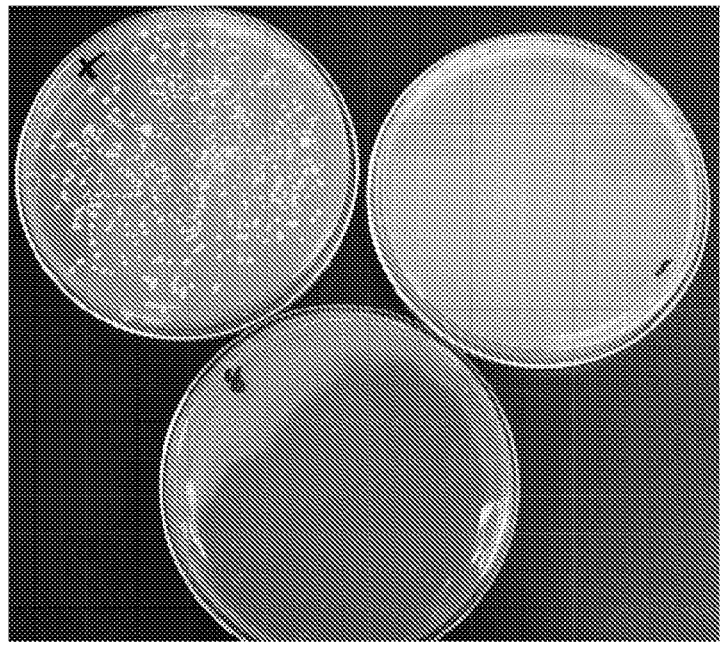
FIG. 3. Targeting dCas9-VP64 with an MS2-VP64 co-activator, a system referred to as DVM, to Act1/g4 severely stunts growth. This image was taken 14 days post transformation. The top left plate shows colony growth from yeast transformed with a control vector that does not target dCas9 to any location. The top right shows a negative control were yeast were mock transformed with water. The bottom plate has colonies from yeast transformed with dCas9-VP64 targeting Act1/g4, a location upstream of the Actin transcriptional start site. Very small pin-point colonies can be seen which did not grow beyond this size.
Figure 5:
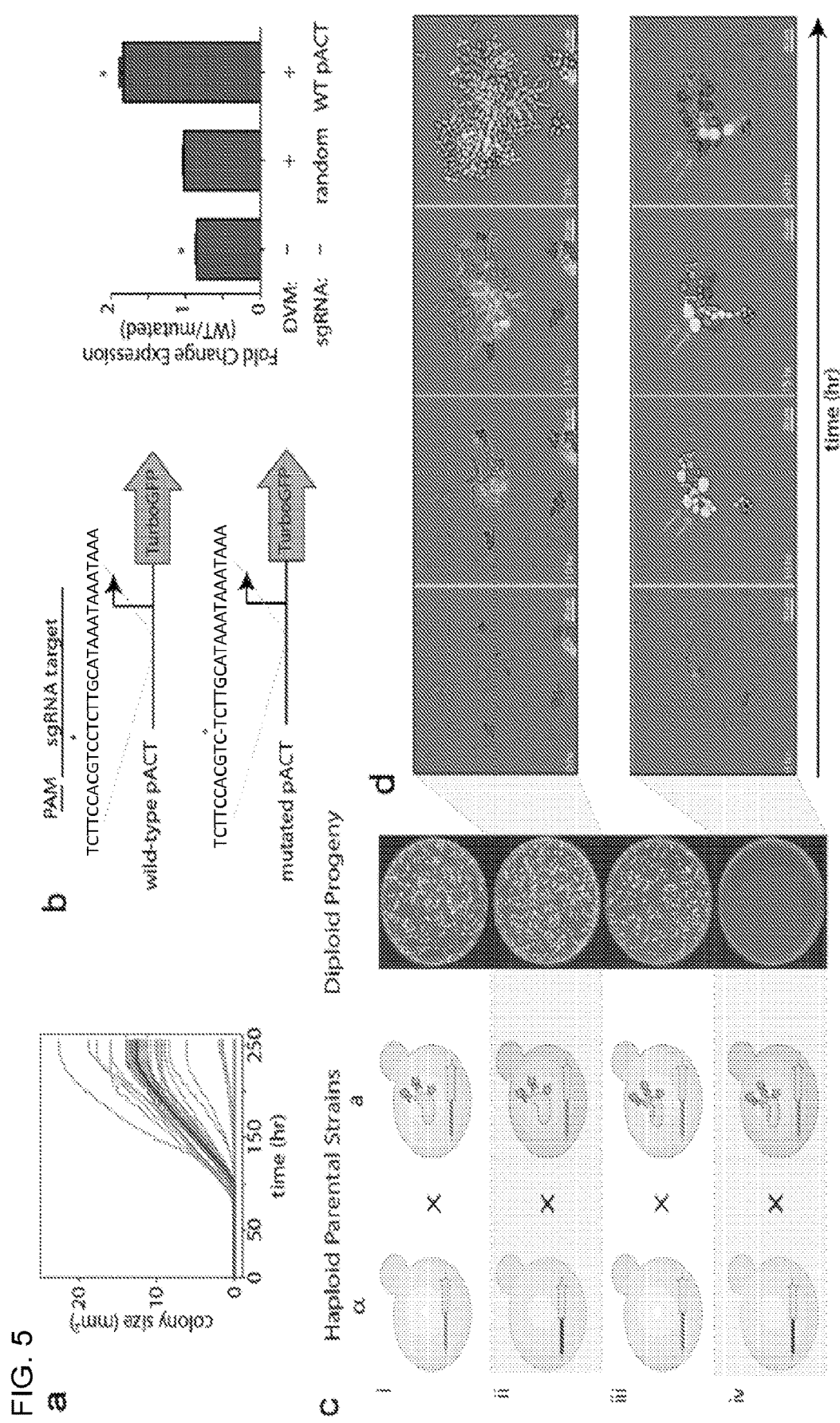
FIG. 5. Engineering speciation by synthetic incompatibility. (A) Growth curves of yeast expressing DVM targeted to promoter regions of SI candidate genes. Random sgRNA control shown in red. Best ACT1 targeting sgRNA in light blue. All others in grey. (n=2, +/−SD, error bars omitted for grey lines for clarity) (B) (Left) Diagram of mutated (SEQ ID NO:20) and wild-type (SEQ ID NO:19) ACT1 promoter-GFP constructs. (Right) GFP expression ratios with or without DVM and/or ACT1 promoter specific sgRNA. (n=3, +/−SD). (C) (Left) Schematic representation of SI components present in haploid strain crosses and (Right) the resulting diploid colonies. (D) Live cell imaging time lapse of diploid cells from crossing RFP+ MATα with GFP+ Mata cells in a compatible (Top) and incompatible (Bottom) mating. Arrows indicate cells which swell and lyse.

S. cerevisiae was transformed with a plasmid that expressed dCas9-VP64, a sgRNA to guide dCas9-VP64 to its target, and K1URA3 for selection on agar plates lacking uracil. Of the 24 plasmids tested, none resulted in a noticeable reduction in growth compared to controls, perhaps because dCas9-VP64 did not sufficiently activate transcription from the selected target loci. Thus, a yeast strain was engineered to express MS2-VP64, which recognizes hairpin structures present in the sgRNA and can boost gene expression. The yeast strain expressing MS2-VP64 (YMM-1) was then transformed with the same set of plasmids, which resulted in stunted growth for several of the targets (Table 2, FIG. 2A). The most striking phenotype resulted from targeting one of the sites upstream of Actin (ACT1/g4). This resulted in no growth after one week and only very slight colonies present after two weeks (FIG. 3). A target site on the bottom strand 190 nucleotides upstream of the ACT1 transcriptional start site resulted in the strongest growth defect with no visible growth after 10 days (FIG. 5A). The nine PAM distal nucleotides are predicted to be Forkhead transcription factor binding sites.

TABLE 2

Growth characteristics of yeast strain YMM-1 transformed with sgRNA directed to the indicated target

| Target/sgRNA | Day 7 Growth (transformation #1) |
| --- | --- |
| TUB2/g1 | Slightly stunted |
| TUB2/g2 | Slightly stunted |
| TUB2/g3 | Stunted Growth |
| TUB2/g4 | Stunted Growth |
| ACT1/g1 | Stunted Growth |
| ACT1/g2 | Larger Colonies than positive control |
| ACT1/g3 | Stunted Growth |
| ACT1/g4 | No growth. |
| ABP1/g1 | Severely Stunted, Barely Visibly Colonies |
| ABP1/g2 | Stunted Growth |
| ABP1/g3 | Slightly stunted |
| ABP1/g4 | Similar to positive control |
| YIP3/g1 | Stunted Growth |
| YIP3/g2 | Slightly stunted |
| YIP3/g3 | Stunted Growth |
| YIP3/g4 | Severely Stunted, Barely Visibly Colonies |
| SWT1/g1 | Stunted Growth |
| SWT1/g2 | Similar to positive control |
| SWT1/g3 | Stunted Growth |
| SWT1/g4 | Similar to positive control |
| COX9/g1 | Similar to positive control |
| COX9/g2 | Stunted Growth |
| COX9/g3 | Similar to positive control |
| COX9/g4 | Similar to positive control |
| No sgRNA (+) Control | Plenty of colonies |
| No DNA (−) Control | No growth |

Figure 8:
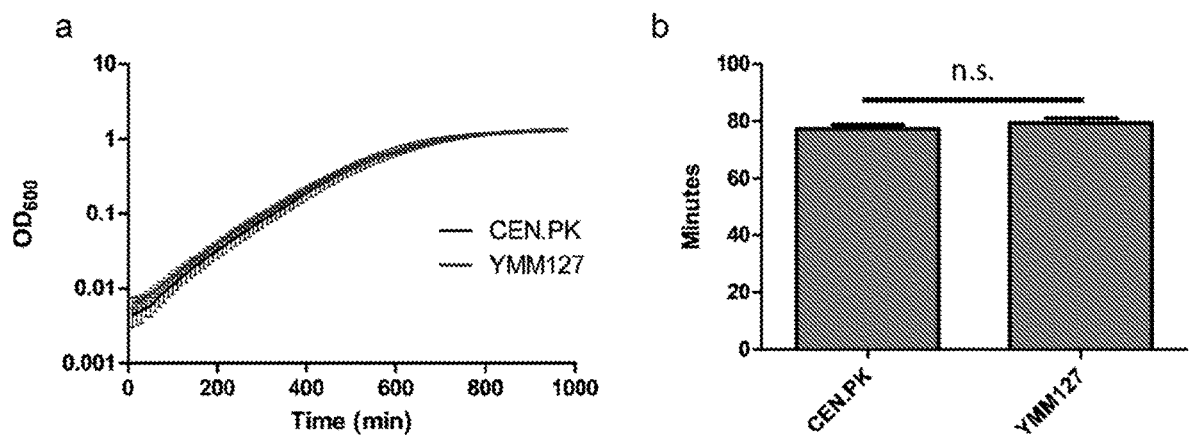
FIG. 8. Determining ACT1 mutation's effect on growth rate. (A) Growth curves shown from strains with a wild-type (CEN.PK) and mutated (YMM127) actin promoters (n=3 independent cultures, mean+/−SEM). (B) Comparison of doubling time between CEN.PK and YMM127 (p>0.05, two tailed t-test).

To generate a synthetically incompatible strain, Cas9 was used to introduce a mutation by non-homologous end joining in the ACT1 promoter. The mutated promoter differs from wild-type by a single cytosine deletion 3 bp upstream of the PAM site. There is no observable growth phenotype resulting from the mutated ACT1 promoter (FIG. 8). Transcription from the mutated promoter was characterized by expressing TurboGFP (Evdokimov et al., 2006. *EMBO Rep.* 7:1006-1012) under the control of the wild-type or mutated ACT1 promoters in the presence and absence of DVM (FIG. 5B). There was a slight increase in TurboGFP expression from the mutated promoter in the absence of DVM. However, no change was found with a non-targeting sgRNA. TurboGFP expression was 1.8-fold higher from the wild-type ACT1 promoter than from the mutated promoter when DVM was guided by an sgRNA targeting the wild-type promoter. Together, these results indicate that the mutation in the ACT1 promoter does not substantially change native expression but prevents targeted transcriptional activation by DVM guided to the wild-type sequence. The DVM targeted to the wild-type ACT1 promoter sequence was then chromosomally integrated into the strain containing the mutated ACT1 promoter to complete constructions of the synthetically incompatible strain (FIG. 2B).

Four additional genes were screened (Table 3), identifying additional targets that stunt growth (Table 4). In order to generate a system that produced lethality, targeting dCas9-VP64 to two targets at once was investigated. Several of the combinations eliminated all growth except for the presence of a handful of colonies that appeared normal (Table 5).

TABLE 3

Additional *S. cerevisiae* overexpression target genes

| Gene | Core Function |
|---|---|
| BEM3 | Cytoskeletal regulation |
| CSE1 | Nuclear trafficking and chromosome segregation |
| DSK2 | Spindle pole duplication |
| MGE1 | Oxidative stress response |

TABLE 4

Growth characteristics of yeast strain YMM-1 transformed with sgRNA directed to the indicated target

| Target/sgRNA | Day 7 Growth |
|---|---|
| BEM3/g1 | Similar to + Control |
| BEM3/g2 | Similar to + Control |
| BEM3/g3 | Similar to + Control |
| CSE1/g1 | Slightly Stunted |
| CSE1/g2 | Similar to + Control |
| CSE1/g3 | Similar to + Control |
| CSE1/g4 | Similar to + Control |
| DSK2/g1 | Slightly Stunted |
| DSK2/g2 | Similar to + Control |
| DSK2/g3 | Slightly Stunted |
| DSK2/g4 | Similar to + Control |
| MGE1/g1 | Similar to + Control |
| MGE1/g2 | Similar to + Control |
| MGE1/g3 | Similar to + Control |
| MGE1/g4 | Similar to + Control |
| No gRNA (+) Control | Plenty of colonies |
| No DNA (−) Control | No growth |

TABLE 5

Growth characteristics of yeast strain YMM-1 transformed with sgRNA directed to the indicated target combinations

| Targets/gRNA | Day 7 growth |
|---|---|
| ACT1/g4 & ABP1/g1 | A couple normal colonies. Many severely stunted colonies. |
| ACT1/g4 & YIP3/g4 | A couple dozen large colonies and many more stunted colonies. |
| ACT1/g4 & DSK2/g2 | A couple small colonies. Otherwise like negative control. |
| ACT1/g4 & MGE1/g3 | Handful of large colonies. Many severely stunted colonies. |
| Act1/g4 | One large colony. Otherwise like negative control. |
| No gRNA (+) control | Lots of large colonies |
| No Plasmid (−) control | No growth. |

The synthetic incompatibility strategy described herein creates a severe penalty to genetic crossing with the wild type. The Act1/g4 target site was mutated in the YMM-1 yeast strain that expresses MS2-VP64; also, dCas9-VP64 targeted to the wild-type Act1/g4 locus was stably integrated into the genome. This did not result in an apparent growth defect (Table 5), indicating that the Act1/g4 mutation in the YMM-1 strain prevents binding of the dCas9-VP64.

Figure 4:
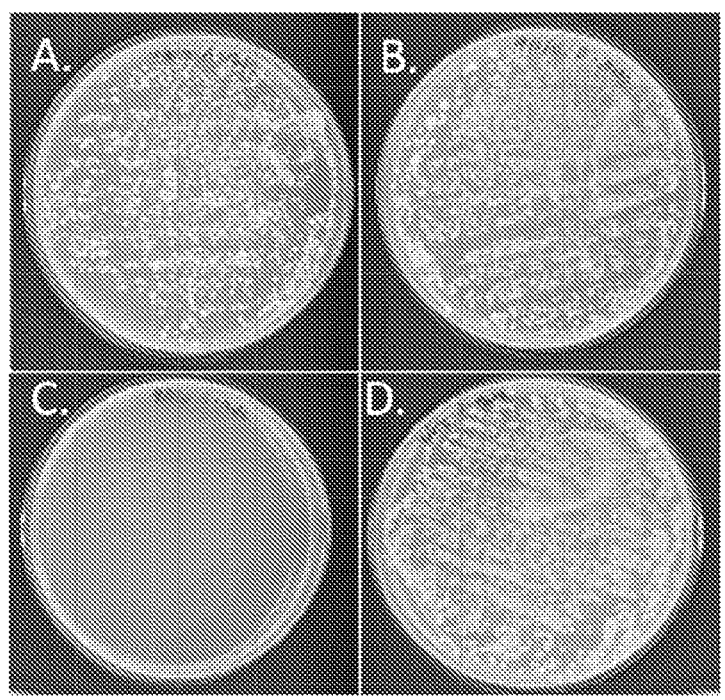
FIG. 4. Yeast were allowed to mate overnight in rich media and then plated on media lacking uracil and leucine to select for diploids. (A) The Mate A plate shows colonies from a cross between two strains which both have mutated Act1/g4 loci. dCas9-VP64 has no genomic target. (B) The Mate B plate demonstrates compatibility between one strain which has a mutated Act1/g4 locus and one with the wild type version. Neither expresses dCas9-VP64. (C) The Mate C plate shows the results of a cross between a strain with a wt Act1/g4 locus and a strain with a mutated Act1/g4 locus expressing dCas9-VP64 targeting the wt Act1/g4. (D) The Mate D plate shows colonies from a cross between two strains with wt Act1/g4 loci.

Next, the genetic compatibility between the synthetically incompatible strain and a strain with the wild-type ACT1 promoter was examined. *S. cerevisiae* has haploid mating types MATa and MATα, and can be propagated as a haploid of either mating type or as a diploid after mating. Two different a-mating type strains and two different α-mating type strains were mated together (Table 6) and plated on media lacking both uracil and leucine to select for diploids (FIG. 2C and FIG. 4).

TABLE 6

Yeast strain information and mating key.

| | Mat-a, ΔAct1/g4, Leucine Auxotroph, DVM | Mat-a, wt Act1/g4, Leucine Auxotroph |
|---|---|---|
| Mat-α, ΔAct1/g4, Uracil Auxotroph | Mate A | Mate B |
| Mat-α, wt Act1/g4, Uracil Auxotroph | Mate C | Mate D |

A genetic cross between a strain with the wild-type Act1/g4 locus and a strain with a mutated Act1/g4 locus expressing MS2-VP64 and dCas9-VP64 targeted to the wild type results in genetic incompatibility (FIG. 4C). When both carry mutated Act1/g4 loci, however, they are genetically compatible (FIG. 4A). Crossing a strain with the mutated Act1/g4 locus with a strain carrying the wild type version in the absence of dCas9-VP64 does not inhibit growth. Together, this demonstrates that the block to sexual reproduction is due to activity of MS2-VP64 and dCas9-VP64 at the wild type Act1/g4 locus.

Mating a MATa strain with the SI genotype but a random sequence sgRNA to a MATα strain also containing the mutated ACT1 promoter resulted in numerous diploid colonies (FIG. 5C, i; FIG. 4A). This shows that expression of the DVM machinery or a mutation in the ACT1 promoter does not prevent sexual reproduction. This same MATa strain was also successfully mated to a MATα strain carrying the wild-type ACT1 promoter (FIG. 2C, ii), as the random sequence sgRNA does not induce lethal overexpression of ACT1. The MATa strain was crossed with a complete synthetically incompatible genotype to a MATα strain with the mutated ACT1 promoter (FIG. 2c, iii). However, when the SI MATa strain was mated with a MATα strain with wild-type ACT1 promoter, diploid colonies were seen only in low frequencies (FIG. 2C, iv; FIG. 4C). This failed mating reflects the genetic incompatibility of the synthetically incompatible genotype with wild-type.

In order to understand the engineered genetic incompatibility on a cellular level, mating experiments were performed and diploid cells were monitored using live cell imaging (FIG. 5D). Diploid yeast resulting from a permissive mating (e.g., FIG. 5C, ii) are able to proliferate and produce a microcolony after 20 hours (FIG. 5D, top). Diploids arising from the non-permissive mating of wild-type ACT1 promoter yeast with the synthetically incompatible strain undergo a limited number of divisions before swelling and eventually lysing (FIG. 5D, bottom). These results are consistent with uncontrolled cytoskeletal growth.

Thus, in one aspect, this disclosure describes a biocontainment/biocontrol system so that the progeny of an organism that possesses the system crossed with a wild-type organism exhibit reduced growth compared to a homozygous wild type organism. Generally, the system involved introducing a genetic barrier to sexual reproduction of a synthetically incompatible (SI) organism with a comparable wild-type organism of the same species. The system involves the use of a programmable transcriptional activator capable of lethal overexpression of one or more endogenous expression-sensitive coding regions. Lethality in the engineered synthetically incompatible strain is prevented by refactoring the target locus, allowing the programmable activator to be expressed in the synthetically incompatible strain. This activator serves as a sentinel for undesired—e.g., synthetically incompatible x wild-type-mating events. Hybridization between the synthetically incompatible strain and an organism containing the transcriptional activator's target sequence results in lethal expression of the expression-sensitive coding region (FIG. 2B).

The biocontainment/biocontrol system can be introduced into a single-celled organism such as, for example, a yeast such as *Saccharomyces cerevisiae*. In other cases, the biocontainment/biocontrol system can be introduced into the cells of a multi-cellular organism such as, for example, a plant or an animal. Exemplary plants into which the biocontainment/biocontrol system may be introduced can include, for example, a field crop (e.g., tobacco, corn, soybean, rice, etc.), a tree (e.g., poplar, rubber tree, etc.), or turfgrass (e.g. creeping bentgrass). Exemplary animals into which the biocontainment/biocontrol system may be introduced can include, for example, an insect (e.g., mosquito, tstetse fly, spotted-wing drosophila, olive fly, gypsy moth, codling moth, deer tick, etc.), a fish (e.g., salmon, carp, sea lamprey, etc.), a mammal (e.g., swine, a mouse, a rat, etc.), an amphibian (e.g., a cane toad, a bullfrog, etc.), a reptile (e.g., brown tree snake, etc.), or a crustacean (e.g., rusty crayfish, etc.).

Thus, when described herein in the context of the biocontainment/biocontrol system being present in a cell, that description encompasses, unless the context dictates otherwise, a single-celled organism, a germ cell of a multicellular organism, or a somatic cell of a multi-cellular organism.

Generally, the biocontainment/biocontrol system includes a genetically-modified cell that includes a coding region whose overexpression decreases growth of the organism, a transcription regulatory region operably linked upstream of the coding region and having a silent mutation, and a polynucleotide that encodes a programmable transcription activator. The programmable transcription activator can be engineered to bind to the transcription regulatory region in the absence of the silent mutation, thereby initiating overexpression of the coding region in the absence of the silent mutation. Thus, in the absence of the silent mutation—i.e., if the organism is crossed with a wild type organism—the transcription activator initiates overexpression of the coding region and limits growth and/or viability of the organism. In the presence of the silent mutation—i.e., when the organism is crossed with another organism having the same biocontainment system—the transcription activator does not initiate overexpression of the coding region and the progeny organisms remain viable.

As used herein, the term "overexpression" refers to a level of transcription of the coding region that is greater than that of a suitable wild-type control. The overexpression of the coding region that occurs when the organism is crossed with a wild-type organism results in altered growth of the organism so that one can identify organisms that are progeny of a cross with a wild type organism. Altered growth can include reduced growth compared to a comparable wild-type organism or can include increased growth compared to a wild-type organism that results is reduced fitness (e.g., a deformity that results in death). Overexpression can refer tp ectopic expression, where genes are expressed in tissues where they are normally silent. Alternatively, or additionally, overexpression can refer to dysregulated expression, where the dynamic expression levels over time are perturbed such as, for example, a coding region that oscillates between an on-state and an off-state in wild-type that is constitutively in the on-state in the mutant.

In some cases, the result of cross between an organism having the biocontainment system and a wild-type organism can result in progeny that do not grow and/or are non-viable. In other cases, the result of cross between an organism having the biocontainment system and a wild-type organism can result in progeny that grow more slowly than organisms homozygous for the biocontainment system and are therefore readily identifiable and may be culled from the population. In still other embodiments, the result of cross between an organism having the biocontainment system and a wild-type organism can result in progeny that grow more rapidly than organisms homozygous for the biocontainment system, but the more rapid growth results in reduced fitness compared to the organisms homozygous for the biocontainment system.

As used herein, a "silent mutation" is a mutation in the DNA of the organism that does not significantly alter the phenotype of the organism outside of its effects within the context of the biocontainment system.

As used herein, the term "programmable transcription activator" refers to a transcription activator whose DNA binding specificity can be programmed. In the context of the biocontainment system described herein, the transcriptional activator is programmed to survey the genome of a cell for the wild-type transcription regulatory sequence that controls transcription of the target coding region, but does not bind to a variant of the transcription regulatory sequence that includes the silent mutation. While described herein in the context of an exemplary embodiment in which the programmable transcription activator is dCas9 fused to the activator domain VP64 and co-expressed with dCas9-VP64, other programmable transcription activators may be used in the biocontainment system. Exemplary alternative programmable transcription activators include, for example, fusions of dCas9, Cas9 (if combined with a short guide RNA), nuclease inactive CPF1, and TALEs to VP64, VP16, VPR, p65, Rta, EDLL, Gal4, TAD, SunTag or any combination thereof. In the case of RNA guided transcriptional regulators (e.g, dCas9-VP64), activation may be boosted by including aptamers in the RNA sequence which allow for the recruitment of aptamer binding protein such as, for example, transcription factor-fusions such as MS2/MCP, PCP, or COM fused to VP64, VP16, VPR, p65, Rta, and EDLL, Gal4, TAD or any combination thereof.

The coding region that is the target for overexpression can be any coding region whose overexpression is detrimental to growth of the organism to a degree sufficient to allow for easy identification of a hybrid cross between an organism having the biocontainment system and a comparable wild-type. In some cases, overexpression of the coding region can result a cross between an organism having the biocontainment system and a comparable wild-type being lethal—e.g., the progeny of the cross do not grow or are otherwise non-viable.

In some cases, the coding region encodes a cytoskeletal polypeptide, an ER-Golgi vesicle polypeptide, an mRNA processing polypeptide, an electron transport polypeptide, a nuclear trafficking polypeptide, a chromosome segregation polypeptide, a spindle pole duplication polypeptide, an oxidative stress polypeptide, a cell-signaling polypeptide, a pro-apoptotic polypeptide or a developmental morphogen polypeptide.

In some cases, an organism may be engineered to include a second biocontainment system involving the programmed overexpression of a second coding region in the absence of a second silent mutation in the transcriptional regulatory region of the second coding region. The second biocontainment system can include a second programmable transcription activator. The second programmable transcription activator may be the same as the first programmable transcription activator in all respects other than the transcription regulatory sequence it is programmed to survey. In other cases, the second transcription activator may include different components that the programmable transcription activator of the first biocontainment system.

Examples

Plasmids and Primers

Figure 6:
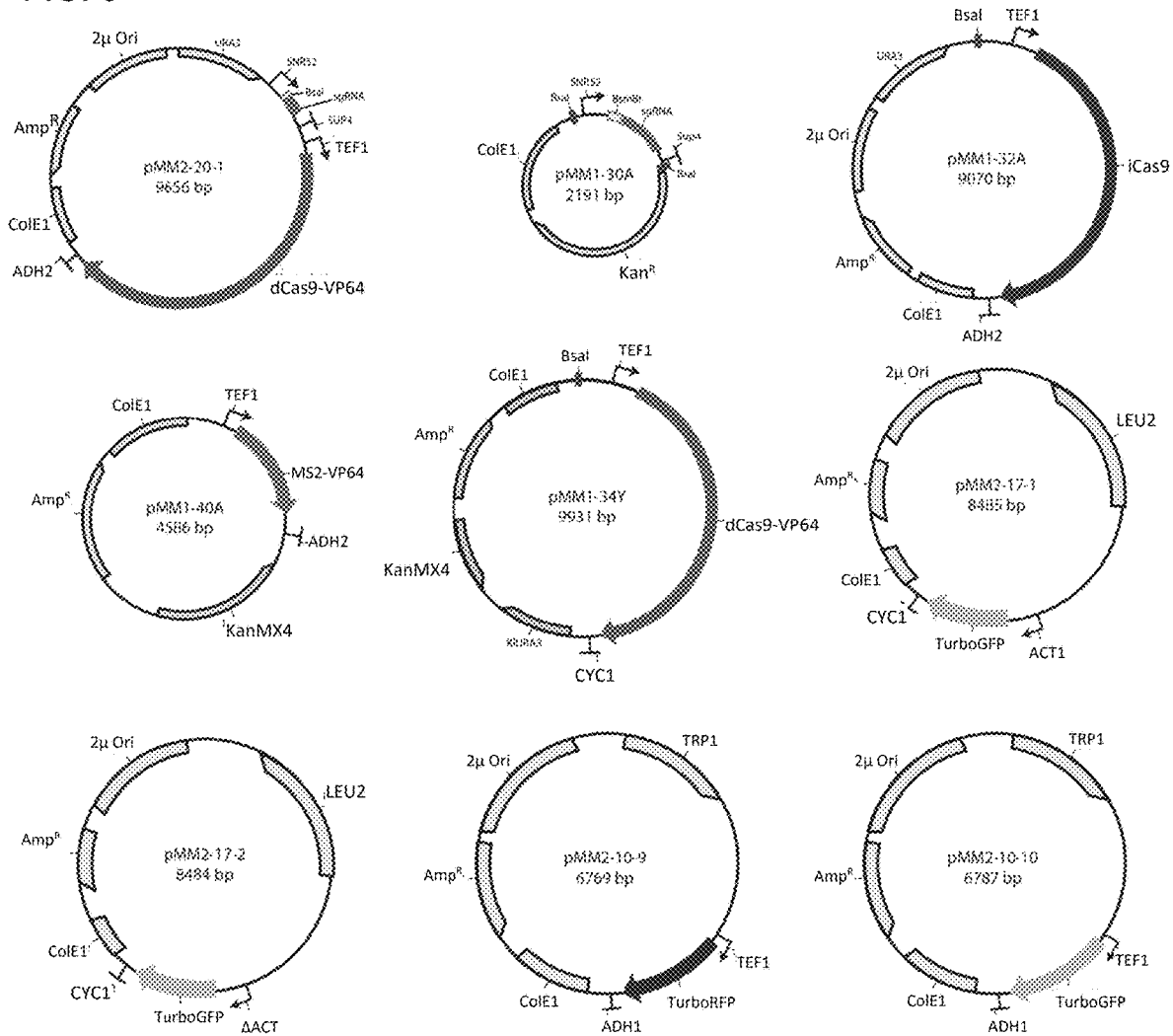
FIG. 6. Plasmid maps of plasmids used herein.

Plasmid maps are shown in FIG. 6 and described in Table 8. Primer sequences are provided in Table 9.

TABLE 8

Plasmids

| Plasmid | Description | Reference | Gen Bank |
|---|---|---|---|
| pMM2-20-1 | Deleterious activation screening plasmid | this study | KX981587 |
| pMM2-20-2 to 20-XX | pMM2-20-1 with spacers 1- to 20-XX XXX | this study | |
| pMM1-30A | sgRNA 2.0 cassette with a BsmbI site for oligos. BsaI releasable. | this study | KX981578 |
| pMM1-32A | iCas9 vector. Contains destination for sgRNA cassettes. | this study | KX981579 |
| pMM1-40A | MS2-VP64 integration cassette template. | this study | KX981582 |
| pMM1-34Y | Integrating dCas9-VP64 cassette. sgRNA cassette destination. | this study | KX981581 |
| pMM2-4A | Template for integrating dCas9-VP64. ACT1 sgRNA. | this study | |
| pMM2-22-2 | Template for integrating dCas9-VP64. Random sgRNA. | this study | |
| pMM2-17-1 | WT pACT1 driven TurboGFP | this study | KX981585 |
| pMM2-17-2 | Mutated pACT1 driven TurboGFP | this study | KX981586 |
| pMM2-10-9 | TurboRFP expression plasmid. | this study | KX981583 |
| pMM2-10-10 | TurboGFP expression plasmid | this study | KX981584 |
| pCRCT | iCas9 source vector. Addgene #60621 | 1 | |
| pICSL80004 | TurboRFP source vector. Addgene #50325 | 2 | |
| pICSL80005 | TurboGFP source vector. Addgene #50322 | 2 | |
| pCORE-UK | KlURA3 and KanMX4 source vector. Addgene #72238 | 3 | |
| M-SPn-VP64 | dCas9-VP64 source[a]. Addgene #48674 | 4 | |
| pESC-Leu | Yeast replicative vector backbone source. | Agilent | |
| MS2-P65-HSF1_GFP | MS2 source plasmid. Addgene #61423 | 5 | |

1 Bao et al., 2014. ACS Synth Biol 4(5): 585-594.
2 Engler et al., 2014. ACS Synth Biol 3(11): 839-843.
3 Storici F and Resnick MA, 2003. Genet Eng 25: 189-207.
4 Esvelt et al., 2013. Nat Methods 10(11): 1116-1121.
5 Konerman et al., 2014. Nature 517(7536)583-588.

TABLE 9

Primers

| Primer | Sequence | SEQ ID NO: |
|---|---|---|
| pMM2-20-16 | | |
| MM_WHI3_3F | GATCAGAGCAGATATCC AATAGTT | 1 |
| MM_WHI3_3R | AAACAACTATTGGATAT CTGCTCT | 2 |
| pMM2-20-4 | | |
| MM_WHI3_4F | GATCGAAAGGGAAAGGA ACTTCTT | 3 |
| MM_WHI3_4R | AAACAAGAAGTTCCTTT CCCTTTC | 4 |
| pMM2-20-28 | | |
| MM_Rando_F | GATCactgtataagact cttcaca | 5 |
| MM_Rando_F | AAACtgtgaagagtctt atacagt | 6 |
| Chromosomal Integration Primers | | |
| MM_TA_LYS_uF | GGCATCGCACAGTTTTA GCGAGGAAAACTCTTCA ATAGTTTTGCCAGCGGC ATAGCTTCAAAATGTTT CTAC | 7 |
| MM_TA_LYS_uR | AATTCATATTTAATTAT TGTACATGGACATATCA TACGTAATGCTCAACCg ggttaattaaggcgc | 8 |
| MM_d64_Leu2_F2 | TTATAGAATTGTGTAGA ATTGCAGATTCCCTTTT ATGGATTCCTAAATCCT CTTTGAAAAGATAATGT ATGATTATG | 9 |
| MM_d64_Leu_R | TGAATTTCATTTATAAA GTTTATGTACAAATATC ATAAAAAAGAGAATCc tcacataatgaaagaga gag | 10 |
| Primers to Identify Genomic Modifications | | |
| MM_TA_CPCR_F | GTTACGTCTATATTCAT TGAAACTGA | 11 |
| MM_Kan_CPCR_R | AACCAAGCATGTCAAGGTC | 12 |
| MM_TA_WT_CPCR_R | ACTCTATATATCAATGCAGCC | 13 |
| MM_WT_Leu2_CPCR_F | TGGCCTCTTCAAGATTATGGA | 14 |
| MM_DV_Leu2_CPCR_F | tattgaaacttgttgaaacgT | 15 |
| MM_DV_Leu2_CPCR_R | CTGTATTCCTTTACATCCTCC | 16 |
| MM_Actg4_CPCR_F | CTACATTCTTCCTTATCGGATCC | 17 |
| MM_Actg4_CPCR_R | AGGAAGAATACAAGAGAGGA | 18 |

Strains and Media

Figure 7:
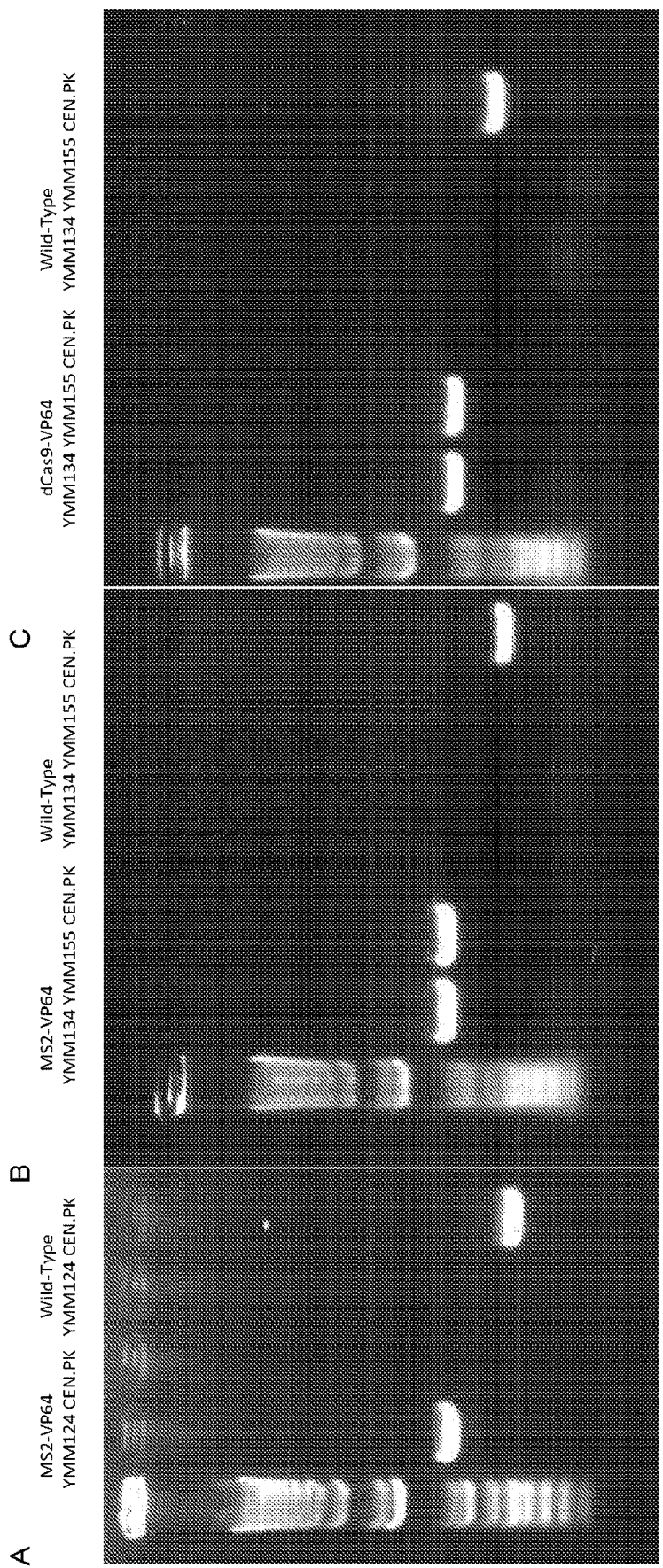
FIG. 7. PCR Verification of Genomic Modifications (A) Results from PCR analysis of Lys2 locus in YMM124 and CEN.PK wild-type control. (B) Results from PCR analysis of Lys2 locus in YMM134, YMM155, and CEN.PK wild-type control. (C) Results from PCR analysis of Leu2 locus in YMM134, YMM155, and CEN.PK wild-type control.

Detailed information for all yeast strains are provided in Table 10 and FIG. 7.

MM_WT_Leu2_CPCR_F and MM_DV_Leu2_CPCR_R which detect the wild-type locus (FIG. 7B). Mutations in the Act1 promoter were detected by PCR amplifying a portion

TABLE 10

Yeast strains

| Name | Genotype | Description |
|---|---|---|
| YMM1[a]/YMM124[b] | MATa, lys2ΔMS2-VP64 KanMX4 | Used for screening growth defects caused by DVM |
| YMM31[a]/YMM125[b] | MAT☐ LEU2 | Wild-type ACT1 promoter strain used for mating experiments |
| YMM27[a] | MATa, KlURA3 | Uracil prototroph |
| YMM134[b] | MATa ACT1-Δ1 lys2ΔMS2-VP64 KanMX4 leu2ΔdCas9-VP64 Random sgRNA KlURA3 | Mutated ACT1 promoter strain carrying DVM guided by random sgRNA |
| YMM139[b] | MAT☐ LEU2 pMM2-10-9 (TurboRFP TRP1) | Fluorescent wild-type ACT1 promoter strain used for live-cell imaging |
| YMM30[a]/YMM141[b] | MAT☐ ACT1-Δ1 LEU2 | Mutated ACT1 promoter strain used for mating experiments |
| YMM35[a]/YMM155[b] | MATa ACT1-Δ1 lys2ΔMS2-VP64 KanMX4 leu2ΔdCas9-VP64 ACT1 sgRNA KlURA3 | Synthetic incompatible strain |
| YMM156[b] | MATa ACT1-Δ1 lys2ΔMS2-VP64 KanMX4 leu2ΔdCas9-VP64 ACT1 sgRNA KlURA3 pMM2-10-10 (TurboGFP TRP1) | TurboGFP positive synthetic incompatible strain |
| YMM157[b] | MATa ACT1-Δ1 lys2ΔMS2-VP64 KanMX4 leu2ΔdCas9-VP64 ACT1 sgRNA KlURA3 pMM2-10-10 (TurboGFP TRP1) | TurboGFP positive mutated ACT1 promoter strain carrying DVM guided by random sgRNA |
| YMM158[b] | MATa pMM2-17-1 (pACT1- TurboGFP LEU2) | No DVM strain with wild-type ACT1 promoter driving TurboGFP |
| YMM159[b] | MATa pMM2-17-2 (pACT1-Δ1-TurboGFP LEU2) | No DVM strain with mutated ACT1 promoter driving TurboGFP |
| YMM160[b] | MATa ACT1-Δ1 lys2ΔMS2-VP64 KanMX4 leu2ΔdCas9-VP64 Random sgRNA KlURA3 pMM2-17-1 (pACT1- TurboGFP LEU2) | Random guide DVM strain with wild-type ACT1 promoter driving TurboGFP |
| YMM161[b] | MATa ACT1-Δ1 lys2ΔMS2-VP64 KanMX4 leu2ΔdCas9-VP64 Random sgRNA KlURA3 pMM2-17-2 (pACT1-Δ1-TurboGFP LEU2) | Random guide DVM strain with mutated ACT1 promoter driving TurboGFP |
| YMM162[b] | MATa ACT1-Δ1 lys2ΔMS2-VP64 KanMX4 leu2ΔdCas9-VP64 ACT1 sgRNA KlURA3 pMM2-17-1 (pACT1- TurboGFP LEU2) | Synthetic incompatible strain with wild-type ACT1 promoter driving TurboGFP |
| YMM163[b] | MATa ACT1-Δ1 lys2ΔMS2-VP64 KanMX4 leu2ΔdCas9-VP64 ACT1 sgRNA KlURA3 pMM2-17-2 (pACT1-Δ1-TurboGFP LEU2) | Synthetic incompatible strain with mutated ACT1 promoter driving TurboGFP |

[a]Strain derived from the S288C (YNN216) background: ura3-52 lys2-801$^{amber}$ ade2-101$^{ochre}$
[b]Strain derived from the CEN.PK background: ura3-52 trp1-289 leu2-3_112 his3 Δ1 MAL2-8C SUC2

Yeast transformations were performed using the Lithium-acetate method (Gietz et al., 2006. *Methods Mol. Biol.* 313:107-120). Chemically competent *E. coli* STBL3 (Thermo Fisher Scientific, Waltham, MA) was used for all plasmid cloning and propagation in LB media (MP) supplemented with appropriate antibiotics. All yeast strains were in the CEN.PKMATa or MATα (van Dijken et al., 2000. *Enzyme Microb. Technol.* 26:706-714) background. Yeast were grown at 28-30° C. on plates or in liquid culture with 250 rpm agitation. Yeast were cultured in YPD (10 g/L yeast extract, 20 g/L peptone, 20 g/L dextrose), 2×YPD, or synthetic dropout (SD) media (1.7 g/L yeast nitrogenous base, 5 g/L ammonium sulfate, yeast synthetic dropout media supplements (Sigma-Aldrich, St. Louis, MO), 20 g/L dextrose). G418 sulfate resistant yeast were selected on YPD agar with 400 μg/ml G418 Sulfate. Counterselection for K1URA3 was performed using 1 g/L 5-florootic acid.

Insertion of the MS2-VP64 cassette in the Lys2 locus was verified by PCR using primers MM_TA_CPCR_F and MM_Kan_CPCR_R which detect the presence of the transgene in the Lys2 locus and MM_TA_CPCR_F and MM_TA_WT_CPCR_R which screen for the wild-type locus. (FIG. 7A). Insertion of the sgRNA and dCas9-VP64 cassette into Leu2 locus was verified by PCR using MM_DV_Leu2_CPCR_F and MM_DV_Leu2_CPCR_R which detect the presence of the transgene and of the promoter using primers MM_Actg4_CPCR_F and MM_Actg4_CPCR_R. The gel purified amplicon was then Sanger sequenced using the MM_Actg4_CPCR_F primer.

Screening Candidate Coding Regions

The screening of target coding regions was performed by transforming yeast strain YMM124 (Table 10) with pMM2-20-1 backbone vectors (Table 8) expressing sgRNA to candidate coding regions (Table 11).

TABLE 11

Target coding regions

| Gene | Function | Overexpression Phenotype [1] |
|---|---|---|
| ACT1 | Actin. Cytoskeletal protein [2]. | Inviable [3] |
| ABP1 | Actin Binding Protein. Cytoskeletal regulation [4]. | Inviable [3] |
| COX9 | Subunit of cytochrome c oxidase [5]. | Inviable [6] |
| SWT1 | Endoribonuclease involved in mRNA quality control [7]. | Inviable [8] |

TABLE 11-continued

Target coding regions

| Gene | Function | Overexpression Phenotype [1] |
|---|---|---|
| TUB2 | β-Tubulin. Cytoskeletal protein [9]. | Inviable [3] |
| WHI3 | Regulator of cell cycle and cell size [10]. | Inviable [10] |
| YIP3 | Vesicular transport protein [11]. | Inviable [12] |

[1] Cherry et al., 2012. *Nucleic Acids Res.*, vol. 40, no. Database issue, pp. D700-705.
[2] Gallwitz D and Seidel R, 1980. *Nucleic Acids Res* 8(5): 1043-1059
[3] Liu et al., 1992. *Genetics* 132(3): 665-673.
[4] Drubin et al., 1988. *J Cell Biol* 107(6): 2551-2561.
[5] Wright et al., 1986. *J Biol Chem* 261(36): 17183-17191.
[6] Sopko et al., 2006. *Mol Cell* 21(3): 319-330.
[7] Röther et al., 2006. *J Biol Chem* 281(48): 36518-36525.
[8] Skružný et al., 2009. *PLoS Biol* 7(1): e1000008.
[9] Neff et al., 1983. *Cell* 33(1): 211-219.
[10] Nash et al., 2001. *Genetics* 157(4): 1469-1480.
[11] Otte et al., 2001. *J Cell Biol* 152(3): 503-518.
[12] Geng et al., 2005. *Eukaryot Cell* 4(7): 1166-1174.

Transformations were plated onto SD-Ura in 6-well plates and incubated at 30° C. To calculate growth rates of colonies on petri dishes, colonies were scanned as they grew using Epson Perfection V19 scanners in two hour intervals for 256 hours (Guillier et al., 2006. *J. Microbiol. Methods* 65:324-334; Baryshnikova et al., 2010. *Nat. Methods* 7:1017-1024). Image analysis was used to track the areas of colonies as they grew. This entailed converting RGB scans into HSV colorspace, selecting the V channel, performing a background subtraction, smoothing, and using a threshold to identify biomass. The V channel was selected because it had the highest contrast with the background. The background was the first image in a time-lapse, before any colonies appeared. Images were smoothed twice with a fine-grain Gaussian filter (sd=1 pixel, filter width=7 pixels) to remove noise. A single threshold was used for all images for consistency.

Colony centers were identified by applying regional peak detection to a z-projection through time using the thresholded images. When colonies merged, these peaks were used to find the dividing line between colonies: the peaks were used as seeds in a watershed on a distance-transformed image. Once colony boundaries were identified, the number of "on" pixels within a boundary at each moment in time was counted as the colony's area. Colonies that fell along the edge of the petri dish, that merged with colonies along the edge, or that had an ambiguous number of peaks within a large merged region were not included in the analysis. To calculate growth rates, the area-over-time data were log-transformed and fit into a line in a 12-hour moving window. The maximum slope in each time series was recorded as that colony's growth rate. The growth rates were analyzed by one-way ANOVA followed by Bonferroni's post-test comparing each condition to the random sgRNA control.

Plate Based Mate Assay

Haploid MATa yeast strain YMM134 and YMM155 were mated to MATα strains YMM125 and YMM141 by combining overnight cultures in YPD to an $OD_{600}$ of 0.1 each in 1 ml YPD. The cultures were then incubated at 30° C. for four hours, washed once with water and 30 µL were plated onto SD-Ura/Leu dropout media.

Flow Cytometry

Flow cytometry was performed using yeast strains YMM158 through YMM163. YMM158, YMM160, and YMM162 expressed TurboGFP driven by the wild-type ACT1 promoter from plasmid pMM2-17-1. YMM159, YMM161, and YMM163 contained pMM2-17-2 and expressed TurboGPF from a mutated ACT1 promoter. Overnight cultures grown in 2 mL SD-Complete media were diluted to an $OD_{600}$=0.5 and grown for an additional four hours. Cells were collected by centrifugation, washed with DPBS, resuspended in DPBS and placed on ice protected from light prior to analysis. Flow cytometry was performed using a LSRFortessa H0081 cytometer. At least 30,000 TurboGFP positive singlet events were collected per sample. The geometric means of GFP fluorescence intensity were compared using one-way ANOVA followed by Tukey's post-test for pairwise comparisons.

Live-Cell Imaging

Yeast strain YMM139 was mated separately with YMM156 and YMM157 in SD-Trp dropout media for 2 hours, pelleted, and resuspended in SD-Ura/Leu/Trp. Mated yeast were loaded onto a CellASIC ONIX diploid yeast plate and supplemented with SD-Ura/Leu/Trp. Cells were imaged using a Nikon Ti-E Deconvolution Microscope System every six minutes for 20 hours.

In the preceding description and following claims, the term "and/or" means one or all of the listed elements or a combination of any two or more of the listed elements; the terms "comprises," "comprising," and variations thereof are to be construed as open ended i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously. The particular examples, materials, amounts, and procedures are to be interpreted broadly in accordance with the scope and spirit of the invention as set forth herein.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A cell of a non-human multicellular organism, the cell comprising a gene expression system that comprises:
   a coding region whose overexpression limits growth or viability of the multicellular organism;
   a transcription regulatory region operably linked upstream of the coding region, and comprising a mutation that provides synthetic incompatibility; and
   a polynucleotide that encodes a programmable transcription activator engineered to bind to the transcription regulatory region in the absence of the mutation, thereby overexpressing the coding region in the absence of the mutation, but does not initiate overexpression of the coding region when the transcription regulatory region comprises the mutation.

2. The cell of claim 1, wherein overexpression comprises ectopic expression or dysregulated expression.

3. The cell of claim 1 wherein the programmable transcription activator comprises dCas9 fused to an activation domain.

4. The cell of claim 1 wherein the coding region encodes a cytoskeletal polypeptide, an ER-Golgi vesicle polypeptide, an mRNA processing polypeptide, an electron transport polypeptide, a nuclear trafficking polypeptide, a chromosome segregation polypeptide, a spindle pole duplication polypeptide, or an oxidative stress polypeptide.

5. The cell of claim 1 wherein the limited multicellular organism viability comprises a decrease in viability of a multicellular organism heterozygous for the gene expression system compared to a suitable control.

6. A method of limiting hybridization of a genetically-modified multicellular organism with a genetically dissimilar variant, the method comprising:
   providing a multicellular organism genetically modified to comprise the gene expression system of claim 1, wherein a cross between the genetically-modified multicellular organism and the genetically dissimilar variant multicellular organism results in progeny that exhibit a phenotype that is distinct from the genetically-modified multicellular organism.

7. The method of claim 6 wherein the genetically dissimilar variant comprises a wild-type multicellular organism.

8. The method of claim 6 wherein the genetically dissimilar variant comprises a different genetic modification compared to the genetically-modified multicellular organism.

9. A method of limiting production, growth or viability of progeny of a genetically-modified multicellular organism with a genetically dissimilar multicellular organism, the method comprising:
   providing a genetically-modified multicellular organism releasable into an environment in which a genetically dissimilar multicellular organisms is present, wherein the genetically-modified multicellular organism comprises the gene expression system of claim 1.

10. The method of claim 9 wherein the genetically-modified organism is male.

11. The method of claim 9, wherein the genetically dissimilar multicellular organism is a wild-type multicellular organism.

12. A germ cell of a non-human multicellular organism comprising:
   a coding region whose overexpression is detrimental to production, growth or viability of progeny of the multicellular organism;
   a transcription regulatory region operably linked to the coding region and comprising a mutation that provides synthetic incompatibility; and
   a polynucleotide engineered to encode a transcription activator that:
      (i) binds to the transcription regulatory region in a cell resulting from a cross between the multicellular organism and a second multicellular organism, wherein the second multicellular organism does not comprise the mutation that provides the synthetic incompatibility, and
      (ii) does not bind to the transcription regulatory region in a cell resulting from a cross between the multicellular organism and a second multicellular organism that comprises the synthetic incompatibility mutation.

13. The germ cell of claim 12 wherein overexpression of the coding region is lethal to progeny of the multicellular organism crossed with a second multicellular organism that lacks the mutation that provides synthetic incompatibility.

14. The germ cell of claim 12, wherein the germ cell is male.

15. The cell of claim 12 wherein the transcription activator comprises dCas9 fused to an activation domain.

16. The cell of claim 12 wherein the coding region encodes a cytoskeletal polypeptide, an ER-Golgi vesicle polypeptide, an mRNA processing polypeptide, an electron transport polypeptide, a nuclear trafficking polypeptide, a chromosome segregation polypeptide, a spindle pole duplication polypeptide, or an oxidative stress polypeptide.

17. The cell of claim 12, further comprising a second gene expression system comprising:
a second coding region whose overexpression decreases growth of the cell or impairs cell division;
a second transcription regulatory region operably linked to the second coding region and comprising a second mutation that provides synthetic incompatibility; and
a polynucleotide that encodes a second programmable transcription activator engineered to bind to the second transcription regulatory region in the absence of the second mutation that provides synthetic incompatibility, thereby overexpressing the second coding region in the absence of the second mutation that provides synthetic incompatibility, but does not initiate overexpression of the second coding region when the second transcription regulatory region comprises the second mutation that provides synthetic incompatibility.

18. The cell of claim 17 wherein the second coding region encodes a cytoskeletal polypeptide, an ER-Golgi vesicle polypeptide, an mRNA processing polypeptide, an electron transport polypeptide, a nuclear trafficking polypeptide, a chromosome segregation polypeptide, a spindle pole duplication polypeptide, or an oxidative stress polypeptide.

19. The cell of claim 12 wherein the coding region, the transcriptional regulatory region, and the mutation providing synthetic incompatibility decrease reproductive fitness of the multicellular organism compared to a suitable control.

20. The cell of claim 19 wherein the suitable control comprises a wild-type cell.

21. The cell of claim 19 wherein the suitable control comprises a cell homozygous for the mutation that provides synthetic incompatibility.

22. A non-human multicellular organism comprising the germ cell of claim 12.

23. The non-human multicellular organism of claim 22, wherein a cross between the multicellular organism and wild-type organism does not result in viable progeny.

24. The non-human multicellular organism of claim 22, wherein the multicellular organism is male.

* * * * *

```
                        SEQUENCE LISTING

Sequence total quantity: 20
SEQ ID NO: 1             moltype = DNA  length = 24
FEATURE                  Location/Qualifiers
source                   1..24
                         mol_type = other DNA
                         organism = synthetic construct
SEQUENCE: 1
gatcagagca gatatccaat agtt                                              24

SEQ ID NO: 2             moltype = DNA  length = 24
FEATURE                  Location/Qualifiers
source                   1..24
                         mol_type = other DNA
                         organism = synthetic construct
SEQUENCE: 2
aaacaactat tggatatctg ctct                                              24

SEQ ID NO: 3             moltype = DNA  length = 24
FEATURE                  Location/Qualifiers
source                   1..24
                         mol_type = other DNA
                         organism = synthetic construct
SEQUENCE: 3
gatcgaaagg gaaaggaact tctt                                              24

SEQ ID NO: 4             moltype = DNA  length = 24
FEATURE                  Location/Qualifiers
source                   1..24
                         mol_type = other DNA
                         organism = synthetic construct
SEQUENCE: 4
aaacaagaag ttcctttccc tttc                                              24

SEQ ID NO: 5             moltype = DNA  length = 24
FEATURE                  Location/Qualifiers
source                   1..24
                         mol_type = other DNA
                         organism = synthetic construct
SEQUENCE: 5
gatcactgta taagactctt caca                                              24

SEQ ID NO: 6             moltype = DNA  length = 24
FEATURE                  Location/Qualifiers
source                   1..24
                         mol_type = other DNA
                         organism = synthetic construct
SEQUENCE: 6
aaactgtgaa gagtcttata cagt                                              24

SEQ ID NO: 7             moltype = DNA  length = 72
FEATURE                  Location/Qualifiers
source                   1..72
                         mol_type = other DNA
                         organism = synthetic construct
SEQUENCE: 7
ggcatcgcac agttttagcg aggaaaactc ttcaatagtt ttgccagcgg catagcttca        60
aaatgtttct ac                                                           72

SEQ ID NO: 8             moltype = DNA  length = 66
FEATURE                  Location/Qualifiers
source                   1..66
                         mol_type = other DNA
                         organism = synthetic construct
SEQUENCE: 8
aattcatatt taattattgt acatggacat atcatacgta atgctcaacc gggttaatta        60
aggcgc                                                                  66
```

```
SEQ ID NO: 9            moltype = DNA   length = 77
FEATURE                 Location/Qualifiers
source                  1..77
                        mol_type = other DNA
                        organism = synthetic construct
SEQUENCE: 9
ttatagaatt gtgtagaatt gcagattccc ttttatggat tcctaaatcc tctttgaaaa    60
gataatgtat gattatg                                                   77

SEQ ID NO: 10           moltype = DNA   length = 71
FEATURE                 Location/Qualifiers
source                  1..71
                        mol_type = other DNA
                        organism = synthetic construct
SEQUENCE: 10
tgaatttcat ttataaagtt tatgtacaaa tatcataaaa aaagagaatc ctcacataat    60
gaaagagaga g                                                         71

SEQ ID NO: 11           moltype = DNA   length = 26
FEATURE                 Location/Qualifiers
source                  1..26
                        mol_type = other DNA
                        organism = synthetic construct
SEQUENCE: 11
gttacgtcta tattcattga aactga                                         26

SEQ ID NO: 12           moltype = DNA   length = 19
FEATURE                 Location/Qualifiers
source                  1..19
                        mol_type = other DNA
                        organism = synthetic construct
SEQUENCE: 12
aaccaagcat gtcaaggtc                                                 19

SEQ ID NO: 13           moltype = DNA   length = 21
FEATURE                 Location/Qualifiers
source                  1..21
                        mol_type = other DNA
                        organism = synthetic construct
SEQUENCE: 13
actctatata tcaatgcagc c                                              21

SEQ ID NO: 14           moltype = DNA   length = 21
FEATURE                 Location/Qualifiers
source                  1..21
                        mol_type = other DNA
                        organism = synthetic construct
SEQUENCE: 14
tggcctcttc aagattatgg a                                              21

SEQ ID NO: 15           moltype = DNA   length = 21
FEATURE                 Location/Qualifiers
source                  1..21
                        mol_type = other DNA
                        organism = synthetic construct
SEQUENCE: 15
tattgaaact tgttgaaacg t                                              21

SEQ ID NO: 16           moltype = DNA   length = 21
FEATURE                 Location/Qualifiers
source                  1..21
                        mol_type = other DNA
                        organism = synthetic construct
SEQUENCE: 16
ctgtattcct ttacatcctc c                                              21

SEQ ID NO: 17           moltype = DNA   length = 23
FEATURE                 Location/Qualifiers
source                  1..23
                        mol_type = other DNA
                        organism = synthetic construct
SEQUENCE: 17
ctacattctt ccttatcgga tcc                                            23

SEQ ID NO: 18           moltype = DNA   length = 22
FEATURE                 Location/Qualifiers
source                  1..22
                        mol_type = other DNA
```

```
                        organism = synthetic construct
SEQUENCE: 18
aggaagaata caagagagag ga                                          22

SEQ ID NO: 19           moltype = DNA   length = 31
FEATURE                 Location/Qualifiers
source                  1..31
                        mol_type = other DNA
                        organism = synthetic construct
SEQUENCE: 19
tcttccacgt cctcttgcat aaataaataa a                                31

SEQ ID NO: 20           moltype = DNA   length = 31
FEATURE                 Location/Qualifiers
misc_difference         1..31
                        note = n is a, c, g, or t
source                  1..31
                        mol_type = other DNA
                        organism = synthetic construct
SEQUENCE: 20
tcttccacgt cntcttgcat aaataaataa a                                31
```